US009568481B2

(12) United States Patent
Snider et al.

(10) Patent No.: US 9,568,481 B2
(45) Date of Patent: Feb. 14, 2017

(54) METHODS OF IDENTIFYING A SUBJECT AS HAVING HEART FAILURE

(75) Inventors: James V. Snider, Pleasanton, CA (US); Sven Jacobson, New York, NY (US)

(73) Assignee: Critical Care Diagnostics, Inc., San Diego, CA (US)

( * ) Notice: Subject to any disclaimer, the term of this patent is extended or adjusted under 35 U.S.C. 154(b) by 0 days.

(21) Appl. No.: 13/282,111

(22) Filed: Oct. 26, 2011

(65) Prior Publication Data

US 2012/0040381 A1    Feb. 16, 2012

Related U.S. Application Data

(63) Continuation of application No. 13/179,173, filed on Jul. 8, 2011, now Pat. No. 8,617,825, which is a continuation of application No. 11/789,169, filed on Apr. 24, 2007, now Pat. No. 7,998,683.

(60) Provisional application No. 60/794,354, filed on Apr. 24, 2006, provisional application No. 60/800,362, filed on May 15, 2006, provisional application No. 60/904,608, filed on Mar. 2, 2007.

(51) Int. Cl.
*G01N 33/68* (2006.01)
*C12Q 1/68* (2006.01)
*G01N 33/564* (2006.01)

(52) U.S. Cl.
CPC ......... *G01N 33/6869* (2013.01); *C12Q 1/6883* (2013.01); *G01N 33/564* (2013.01); *G01N 33/6893* (2013.01); *G01N 2333/54* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,208,479 A * | 6/1980 | Zuk et al. ............... 435/7.9 |
| 5,206,140 A | 4/1993 | Marder et al. | |
| 5,786,163 A | 7/1998 | Hall | |
| 6,040,147 A | 3/2000 | Ridker et al. | |
| 6,210,976 B1 | 4/2001 | Sabbadini | |
| 6,288,218 B1 | 9/2001 | Levinson | |
| 6,323,334 B1 | 11/2001 | Kingsbury et al. | |
| 6,810,284 B1 * | 10/2004 | Bradley ................... 600/510 |
| 6,905,827 B2 | 6/2005 | Wohlgemuth et al. | |
| 7,087,396 B2 | 8/2006 | Tominaga et al. | |
| 7,432,060 B2 | 10/2008 | Lee | |
| 7,655,415 B2 | 2/2010 | Lee | |
| 7,670,769 B2 | 3/2010 | Lee | |
| 7,985,558 B2 | 7/2011 | Lee | |
| 7,989,210 B2 | 8/2011 | Lee | |
| 7,998,683 B2 | 8/2011 | Snider et al. | |
| 8,090,562 B2 | 1/2012 | Snider et al. | |
| 8,420,785 B2 | 4/2013 | Snider et al. | |
| 8,530,173 B2 | 9/2013 | Lee | |
| 8,597,958 B2 | 12/2013 | Lee | |
| 8,617,825 B2 | 12/2013 | Snider et al. | |
| 8,734,769 B2 | 5/2014 | Lee | |
| 8,748,116 B2 | 6/2014 | Lee | |
| 2002/0115081 A1 | 8/2002 | Lee et al. | |
| 2003/0124624 A1 | 7/2003 | Tominaga et al. | |
| 2003/0228570 A1 | 12/2003 | Yat Wah Tom et al. | |
| 2004/0048286 A1 | 3/2004 | Lee | |
| 2004/0121343 A1 | 6/2004 | Buechler et al. | |
| 2004/0132013 A1 | 7/2004 | DeBold | |
| 2004/0133079 A1 | 7/2004 | Mazar et al. | |
| 2005/0130136 A1 | 6/2005 | Lee | |
| 2005/0196817 A1 | 9/2005 | Kingsmore et al. | |
| 2005/0203046 A1 | 9/2005 | Schmitz et al. | |
| 2005/0250156 A1 | 11/2005 | Shebuski | |
| 2005/0272054 A1 | 12/2005 | Cargill et al. | |
| 2006/0216755 A1 | 9/2006 | Lee | |
| 2007/0042978 A1 | 2/2007 | Girard et al. | |
| 2007/0248981 A1 | 10/2007 | Snider et al. | |
| 2008/0003199 A1 | 1/2008 | Lee | |
| 2009/0192078 A1 | 7/2009 | Lee | |
| 2009/0264779 A1 | 10/2009 | Snider et al. | |
| 2009/0305265 A1 | 12/2009 | Snider et al. | |
| 2010/0009356 A1 | 1/2010 | Snider et al. | |
| 2010/0055683 A1 | 3/2010 | Snider et al. | |
| 2011/0053170 A1 | 3/2011 | Snider et al. | |
| 2011/0250703 A1 | 10/2011 | Lee | |
| 2011/0256635 A1 | 10/2011 | Snider | |
| 2011/0262941 A1 | 10/2011 | Snider et al. | |
| 2012/0040381 A1 | 2/2012 | Snider et al. | |
| 2012/0065897 A1 | 3/2012 | Snider et al. | |
| 2012/0276551 A1 | 11/2012 | Snider | |
| 2013/0071404 A1 | 3/2013 | Snider et al. | |
| 2013/0177931 A1 | 7/2013 | Snider et al. | |

(Continued)

FOREIGN PATENT DOCUMENTS

| | | |
|---|---|---|
| EP | 1731910 | 12/2006 |
| JP | 2005-291899 | 10/2005 |

(Continued)

OTHER PUBLICATIONS

Ridker et al. (England J. Medicine 2000 vol. 342, p. 836-843).*
Morrison et al. (American College of Cardiology 2002 vol. 39, p. 202-209).*
Shimpo et al. Circulation 2004 vol. 109, p. 2186-2190.*
Moe et al. Am. Heart J. 2000 vol. 139, p. 587-595.*
Hall et al. Circulation 1994 vol. 89, p. 1934-1942.*
Yasue et al. Circulation 1994, vol. 90, p. 195-203.*
Oh et al. (J. Am. Coll. Cardiol. 2006 vol. 47, p. 500-506).*
U.S. Appl. No. 13/151,012, filed Jun. 1, 2011, Lee.
Albert et al., "Prospective study of C-reactive protein, homocysteine, and plasma lipid levels as predictors of sudden cardiac death," Circulation 105(22):2595-2599 (2002).

(Continued)

*Primary Examiner* — Jacob Cheu
(74) *Attorney, Agent, or Firm* — Fish & Richardson P.C.

(57) ABSTRACT

Measurement of circulating ST2 and/or IL-33 concentrations is useful for the prognostic evaluation of subjects, in particular for the prediction of adverse clinical outcomes, e.g., mortality, and the detection of severe disease.

24 Claims, 11 Drawing Sheets

(56) References Cited

U.S. PATENT DOCUMENTS

| | | |
|---|---|---|
| 2013/0244236 A1 | 9/2013 | Snider et al. |
| 2013/0251664 A1 | 9/2013 | Lee |
| 2013/0273562 A1 | 10/2013 | Lee |
| 2013/0317030 A1 | 11/2013 | Lee |
| 2013/0345805 A1 | 12/2013 | Snider et al. |
| 2014/0045200 A1 | 2/2014 | Snider et al. |
| 2014/0051773 A1 | 2/2014 | Snider |
| 2014/0058743 A1 | 2/2014 | Snider et al. |

FOREIGN PATENT DOCUMENTS

| | | |
|---|---|---|
| WO | 00/35473 | 6/2000 |
| WO | 00/35951 | 6/2000 |
| WO | 00/73498 | 12/2000 |
| WO | 01/70817 | 9/2001 |
| WO | 02/38794 | 5/2002 |
| WO | WO 03/094856 | 11/2003 |
| WO | 03/100000 | 12/2003 |
| WO | 2004/056868 | 7/2004 |
| WO | 2005/041893 | 5/2005 |
| WO | 2005/079844 | 9/2005 |
| WO | 2007/127749 | 11/2007 |
| WO | 2007/130627 | 11/2007 |
| WO | 2007/130962 | 11/2007 |
| WO | 2007/131031 | 11/2007 |
| WO | 2007/143295 | 12/2007 |
| WO | 2009/129454 | 10/2009 |
| WO | 2011/127412 | 10/2011 |
| WO | 2011/127412 | 11/2011 |

OTHER PUBLICATIONS

Anwaruddin et al., "Renal function, congestive heart failure, and amino-terminal pro-brain natriuretic peptide measurement: results from the ProBNP investigation of dyspnea in the Emergency Department (PRIDE) Study," J. Am. Coll. Cardiol. 47(1):91-97 (2006).
Auer et al., "C-reactive protein and coronary artery disease," Jpn Heart J. 43(6):607-619 (2002).
Baekkevold et al., "Molecular characterization of NF-HEV, a nuclear factor preferentially expressed in human high endothelial venules," Am. J. Path. 163(1):69-79 (2003).
Baggish et al., "A validated clinical and biochemical score for the diagnosis of acute heart failure: The ProBNP Investigation of Dyspnea in the Emergency Department (PRIDE) Acute Heart Failure Score," Am. Heart J. 151:48-54 (2006).
Baumgarten et al., "Cytokines as emerging targets in the treatment of heart failure," Trends Cardiovasc Med. 10(5):216-223 (2000).
Bayes-Genis Antoni, "The circulating NTproBNP level, a new biomarker for the diagnosis of heart failure in patients with acute shortness of breath," Revista Espanola de Cardiolgiz 58(10):1142-1144 (2005).
Blum et al., "Pathophysiological role of cytokines in congestive heart failure," Annu. Rev. Med. 52:15-27 (2001)(Abstract).
Boisot et al., "Serial Sampling of ST2 Predicts 90-Day Mortality Following Destabilized Heart Failure," Journal of Cardiac Failure 14:732-738 (2008).
Brint et al., "ST2 is an inhibitor of interleukin 1 receptor and Toll-like receptor 4 signaling and maintains endotoxin tolerance," Nat. Immunol. 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med. 30(7):1468-1473 (2004).
Carter et al., "Regulation of ST2L expression of T helper (Th) type 2 cells," Eur. J. Immunol. 31(10):2979-2985 (2001)(Abstract only).
Chan et al., "Human IL-18 receptor and ST2L are stable and selective markers for the respective type 1 and type 2 circulating lymphocytes," J. Immunol 167(3):73-75 (2005).

Conklin, B. "B-type Natriuretic peptide: a new measurement to distinguish cardiac from pulmonary causes of actue dyspnea," Journal fo Emergency Nursing 31(1):73-75 (2005).
Coyle et al., "Crucial role of the interleukin 1 receptor family member T1/ST2 in T helper cell type 2-mediated lung mucosal immune responses," J. Exp. Med. 190(7):895-902 (1999).
Dhalla et al., "Measurement of adrenolutin as an oxidation product of catecholamines in plasma," Mol. Cell. Biochem. 87:85-92 (1989).
ELECSYS® ProBNP assay, Roche Diagnostics, Indianapolis, IN, package insert v.7, Jul. 2007.
Feldman et al., "C-reactive protein is an independent predictor of mortality in women with HIV-1 infection," J. Acquir. Immune Defic. Syndr. 32(2):210-214 (2003)(abstract).
Figal et al., "Usefulness of NTproBNP in the emergency management of patients with severe dyspnea and an uncertain heart failure diagnosis", Revista Espanola de Cardiologia 58(10):1155-1161 (2005).
Forssmann et al., "The heart is the center of a new endocrine, paracrine, and neuroendocrine system," Arch. Histol. Cytol. 52 Suppl:293-315 (1989)(Abstract).
Galvani et al., "Prognostic influence of elevated values of cardiac troponin I in patients with unstable angina," Circulation 95(8):2053-2059 (1997)(Abstract).
Gegenhuber et al., "B-type natriuretic peptide and amino terminal proBNP predict one-year mortality in short of breath patients independently of the baseline diagnosis of acute destabilized heart failure," Clinica Chimica Acta 370(1-2):174-179 (2006).
GenBank Acc. No. NM_003856.2, Jan. 24, 2003.
GenBank Acc. No. NM_016232.4, Jan. 24, 2003.
GenBank Acc. No. NM_033439.2, Aug. 31, 2004.
GenBank Acc. No. NP_003847.2, Jan. 24, 2003.
GenBank Acc. No. NP_057316.3, Jan. 24, 2003.
GenBank Acc. No. NP_254274.1, Sep. 12, 2001.
Goetze et al., "B-type natriuretic peptide and its precursor in cardiac venous blood from failing hearts," European Journal of Heart Failure 7(1):69-74 (2005).
Gwechenberger et al., "Cardiac myocytes produce interleukin-6 in culture and in viable border zone of reperfused infarctions," Circulation 99(4):546-551 (1999).
Heeschen et al., "Predictive value of C-reactive protein and troponin T in patients with unstable angina: a comparative analysis. CAPTURE Investigators. Chimeric c7E3 antiPlatelet therapy in unstable angina refractory to standard treatment trial," J Am. Coll Cardiol. 35(6):1535-1542 (2000)(Abstract only).
Information Hyperlinked Over Proteins—Symbol IL1RL1, 2006.
Iwahana et al., "Different promoter usage and multiple transcription initiation sites of the interleukin-1 receptor-related human ST2 gene in UT-7 and TM12 cells," Eur. J. Biochem. 264(2):397-406 (1999).
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol. 50:607-613 (2007).
Januzzi et al., "Natriuretic peptide testing for the evaluation of critically ill patients with shock in the intensive care unit: a prospective cohort study," Crit. Care 10(1):R37 (2006).
Januzzi et al., "NT-proBNP testing for diagnosis and short-term prognosis in acute destabilized heart failure: an international pooled analysis of 1256 patients: the International Collaborative of NT-proBNP Study," Eur. Heart J. 27(3):330-337 (2006).
Januzzi et al., "The N-terminal Pro-BNP investigation of dyspnea in the emergency department (PRIDE) study," Am. J. Cardiol. 95(8):948-954 (2005).
Januzzi et al., "The value of soluble ST2 measurement for the diagnostic and prognostic evaluation of patients with acute dyspnea," Circulation 114(18):721 (2006)(Abstract).
Januzzi et al., "Utility of amino-terminal pro-brain natriuretic peptide testing for prediction of 1-year mortality in patients with dyspnea treated in the emergency department," Arch. Intern. Med. 166(3):315-320 (2006).
Kakkar et al., "The IL-33/ST2 pathway: Therapeutic target and novel biomarker," Nature Reviews Drug Discovery 7(10):827-840 (2008).

(56) References Cited

OTHER PUBLICATIONS

Kida et al., "Pathophysiological role of natriuretic peptides," Rinsho Byori 37(8):875-882 (1989)(Abstract only).
Kieser et al., "Identification of the primary growth response gene, ST2/T1, as a gene whose expression is differentially regulated by different protein kinase C isozymes," FEBS Lett. 372(2-3):189-193 (1995).
Knudsen et al., "Predictors of elevated B-type natriuretic peptide concentrations in dyspneic patients without heart failure: an analysis from the breathing not properly multinational study," Ann. Emerg. Med. 45(6):573-580 (2005).
Krauser et al., "Effect of body mass index on natriuretic peptide levels in patients with acute congestive heart failure: a ProBNP Investigation of Dyspnea in the Emergency Department (PRIDE) substudy," Am. Heart J. 149(4):744-750 (2005).
Kumar et al., "Expression of ST2, an interleukin-1 receptor homologue, is induced by proinflammatory stimuli," Biochem. Biophys. Res. Com. 235(3):474-478 (1997).
Kumar et al., "ST2/T1 protein functionally binds to two secreted proteins from Balb/c 3T3 and human umbilical vein endothelial cells but does not bind interleukin 1," J. Biol. Chem. 270(46):27905-27913 (1995).
Kuroiwa et al., "Construction of ELISA system to quantify human ST2 protein in sera of patients," Hybridoma 19(2):151-159 (2000).
Kuroiwa et al, "Identification of human ST2 protein in the sera of patients with autoimmune diseases," Biochemical and Biophysical Research Communications 284:1104-1108 (2001).
Lammerding et al., "Mechanotransduction in cardiac myocytes", Ann. NY Acad. Sci. 1015:53-70, May 2004.
Lee et al., "Novel markers for heart failure iagnosis and prognosis", Curr. Opin. Cardiol. 20(3):201-210 (2005).
Leyva et al., European Heart J. 19:1814-1822 (1998).
Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A. 95(12):6930-6935 (1998).
Macgowan et al., "Circulating interleukin-6 in severe heart failure", Am. J. Cardiol. 15;79(8):1128-31 (Apr. 1997).
Mackenna et al., "Role of mechanical factors in modulating cardiac fibroblast function and extracellular matrix synthesis," Cardiovasc Res. 46(2):257-63 (May 2000).
Maisel et al., "Bedside B-Type Natriuretic Peptide in the Emergency Diagnosis of Heart Failure With Reduced or Preserved Ejection Fraction," J. Am. Coll. Cardiol. 41:2010-2017 (2003).
Maisel et al., "Primary results of the Rapid Emergency Department Heart Failure Outpatient Trial (REDHOT). A multicenter study of B-type natriuretic peptide levels, emergency department decision making, and outcomes in patients presenting with shortness of breath," J. Am. Coll. Cardiol. 44(6):1328-1333 (2004).
Maisel et al., "Rapid measurement of B-type natriuretic peptide in the emergency diagnosis of heart failure," N. Engl. J. Med. 347(3):161-167 (2002).
Mann et al., "Stress activated cytokines and the heart," Cytokine Growth Factor Rev. 7(4):341-54 (Dec. 1996).
McCord et al., "Relationship between obesity and B-type natriuretic peptide levels," Arch. Intern. Med. 164(20):2247-2252 (2004).
McCullough et al., "B-type natriuretic peptide and renal function in the diagnosis of heart failure: an analysis from the Breathing Not Properly Multinational Study," Am. J. Kidney Dis. 41(3):571-579 (2003).
Millenium Pharmaceuticals, Inc. "Millenium Pharmaceuticals identifies a key mediator of allergic immune response," Press Release Oct. 4, 1999 (2 pages).
Mitcham et al., "T1/ST2 signaling establishes it as a member of an expanding interleukin-1 receptor family," J. Biol. Chem. 271(10):5777-83 (Mar. 8, 1996).
Moe et al., "Neurohormonal activation in severe heart failure: relations to patient death and the effect of treatment with flosequinan," Am. Heart. J. 139:587-95 (2000).
Monoclonal Antibody: Anti-Human ST2; Medical & Bioligical Laboratories Co., Ltd., Aug. 23, 2000 (2 pages).
Mueller et al., "Increased Plasma Concentrations of Soluble ST2 are Predictive for 1-Year Mortality in Patients with Acute Destabilized Heart Failure," Clinical Chemistry 54:752-756 (2008).
Mueller et al., "Use of B-type natriuretic peptide in the evaluation and management of acute dyspnea," New England Journal of Medicine 350(7):647-654 (2004).
Mukoyama et al., "Augmented secretion of brain natriuretic peptide in acute myocardial infarction," Biochem. Biophys. Res. Commun. 180(1):431-6 (Oct. 15, 1991)(Abstract).
Murphy et al., "Signaling and transcription in T helper development," Annu Rev Immunol 18:451-94 (2000).
Ng et al., "Diagnosis of heart failure using urinary natriuretic peptides," Clin Sci (Lond). 106(2):129-33 (Feb. 2004).
Nozaki et al., "Soluble tumor necrosis factor receptors are elevated in relation to severity of congestive heart failure," Jpn. Circ. J. 61:657-64 (1997).
O'Neill et al., "The IL-1 receptor/toll-like receptor superfamily: crucial receptors for inflammation and host defense," Immunol Today 21(5):206-9 (2000).
Ohki et al., "Identification of mechanically induced genes in human monocytic cells by DNA microarrays," J. Hypertens 20(4):685-691 (2002).
Ohtsuka et al., "Effect of beta-blockers on circulating levels of inflammatory and anti-inflammatory cytokines in patients with dilated cardiomyopathy," J. Am. Coll. Cardiol. 37(2):412-7 (2001).
Onda et al., "Identification of genes differentially expressed in canine vasospastic cerebral arteries after subarachnoid hemorrhage," Journal of Cerebral Blood Flow & Metabolsim 19:1279-1288 (1999).
Orus et al., "Prognostic value of serum cytokines in patients with congestive heart failure," J. Heart Lung Transplant 19:419-25 (2000).
Oshikawa et al., "Acute eosinophilic pneumonia with increased soluble ST2 in serum and bronchoalveolar lavage fluid," Respir. Med. 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Oshikawa et al., "Expression and function of the ST2 gene in a murine model of allergic airway inflammation," Clin. Exp. Allergy 32(10):1520-1526 (2002).
Oshikawa et al., "Expression of ST2 in helper T lymphocytes of malignant pleural effusions," Am. J. Respir. Crit. Care Med. 165(7):1005-1009 (2002).
Oshikawa et al., "ST2 protein induced by inflammatory stimuli can modulate acute lung inflammation," Biochem. Biophys. Res. Commun. 299(1):18-24 (2002).
Perrier et al., Am. J. Respir. Crit. Care Med. 156(2):492-496 (1997).
Potter et al., "Mutations in the murine fitness 1 gene result in defective hematopoiesis," Blood 90(5):1850-7 (1997).
Richards et al., "Plasma N-terminal pro-brain natriuretic peptide and adrenormedullin: new neurohormonal predictors of left ventricular function and prognosis after myocardial infarction," Circulation 97:1921-1929 (1998).
Ridker et al., "Inflammation, aspirin, and the risk of cardiovascular disease in apparently healthy men," New England J. Med. 336:973-979 (1997).
Rohde et al., "Circulating cell adhesion molecules are correlated with ultrasound-based assessment of carotid atherosclerosis," Arterial Sclerotic Vasc. Biol. 18:1765-1770 (1998).
Rohde et al., "Plasma concentrations of interleukin-6 and abdominal aortic diameter among subjects without aortic dilatation," Arterial Sclerotic Vasc. Biol. 19:1695-1699 (1999).
Roig et al., "Serum interleukin-6 in congestive heart failure secondary to idiopathic dilated cardiomyopathy," Am. J. Cardiol. 82(5):688-90, A8 (1998).
Sabatine et al., "Multimarker approach to risk stratification in non-ST elevation acute coronary syndromes: simultaneous assessment of troponin I, C-reactive protein, and B-type natriuretic peptide," Circulation 105(15):1760-1763 (2002).

(56) References Cited

OTHER PUBLICATIONS

Saccani et al., "Divergent effects of LPS on expression of IL-1 receptor family members in mononuclear phagocytes in vitro and in vivo," Cytokine 10(10):773-80 (1998).
Schmitz et al., "IL-33, an interleukin-1-like cytokine that signals via the IL-1 receptor-related protein ST2 and induces T helper type 2-associated cytokines," Immunity 23(5):479-490 (2005).
Selvais et al., J. Card. Fail. 6(3):201-7 (2000)(Abstract only).
Shimizu et al., "Functional SNPs in the distal promoter of the ST2 gene are associated with atopic dermatitis," Hum. Mol. Genet. 14(19):2919-2927 (2005).
Shimpo et al., "Serum levels of the interleukin-1 receptor family member ST2 predict mortality and clinical outcome in acute myocardial infarction" Circulation 109(18):2186-2190 (2004).
Silver et al., Cong. Heart Fail. 10(5 suppl. 3):1-30 (2004).
Sims JE, "IL-1 and IL-18 receptors, and their extended family," Current Opinion in Immunology 14:117-122 (2002).
Strunk et al., "Impact of the history of congestive heart failure on the utility of B-type natriuretic peptide in the emergency diagnosis of heart failure: results from the Breathing Not Properly Multinational Study," Am. J. Med. 119(1):69 e1-11 (2006).
Sussamn et al., "Dance band on the Titanic: Biomechanical signaling in cardiac hypertrophy," Circ. Res. 91(10):888-98 (2002).
Svensson et al., "Prognostic value of biochemical markers, 12-lead ECG and patient characteristics amongst patients calling for an ambulance due to a suspected acute coronary syndrome," Journal of Internal Medicine 255(4):469-477 (2004).
Tajima et al., "The increase in serum soluble ST2 protein upon acute exacerbation of idiopathic pulmonary fibrosis," Chest 124(4):1206-1214 (2003).
Tang et al., "Gene expression profiling during the transition to failure in TNF-αover-expressing mice demonstrates the development of autoimmune myocarditis," Journal of Molecular and Cellular Cardiology 36:515-30 (2004).
Tominaga et al., "Nucleotide sequence of a complementary DNA for human ST2," Biochim. Biophys. Acta. 1171:215-218 (1992).
Tominaga et al., "ST2 gene: a gene that is induced by growth stimulation and encoding a product highly similar to the interleukin 1 receptors," Seikagaku 67(5):356-64 (1995)(Japanese with translation).
Tominaga, FEBS Lett., "A putative protein of a growth specific cDNA from BALB/c-3T3 cells is highly similar to the extracellular portion of mouse interleukin 1 receptor," 258:301-304 (1989).
Townsend et al., "T1/ST2-deficient mice demonstrate the importance of T1/ST2 in developing primary T helper cell type 2 responses," J. Exp. Med. 191(6):1069-76 (2000).
Tsuchiya et al., "Th1, Th2 and activated T-cell marker and clinical prognosis in peripheral T-cell lymphoma unspecified comparison AILD, ALCL, lymphoblastic lymphoma and ATLL," Blood 103:236-241 (2004).
Tsutamoto et al., "Interleukin-6 spillover in the peripheral circulation increases with the severity of heart failure, and the high plasma level of interleukin-6 is an important prognostic predictor in patients with congestive heart failure," J. Am. Coll. Cardiol. 31(2):391-8 (1998).
Tung et al., "Utility of B-type natriuretic peptide for the evaluation of intensive care unit shock," Crit. Care Med. 32(8):1643-1647 (2004).
Van Kimmenade et al., "Utility of amino-terminal pro-brain natriuretic peptide, galectin-3, and apelin for the evaluation of patients with acute heart failure," J. Am. Coll. Cardiol. 48(6):1217-24 (2006).
Vidal et al., "Prognostic value of cytokines and neurohormones in severe heart failure," Rev. Esp. Cardiol. 55(5):481-6 (2002).
Wang et al., "Expression of interleukin-1β, interleukin-1 receptor, and interleukin-1 receptor antagonist mRNA in rat carotid artery after balloon angioplasty," Biochem. Biophyl. Res. Comm. 271:138-143 (2000).

Weinberg et al., "Expression and regulation of ST2, an interleukin-1 receptor family member, in cardiomyocytes and myocardial infarction," Circulation 106(23):2961-2966 (2002).
Weinberg et al., "Identification of serum soluble ST2 receptor as a novel heart failure biomarker," Circulation 107(5):721-726 (2003).
Yamaoka et al., "Anti-inflammatory cytokine profile in human heart failure: behavior of interleukin-10 in association with tumor necrosis factor-alpha," Jpn. Circ. J. 63(12):951-6 (1999).
Yanagisawa et al., "Murine ST2 gene is a member of the primary response gene family induced by growth factors," FEBS Lett. 302(1):51-53 (1992).
Yanagisawa et al., "Presence of a novel primary response gene ST2L, encoding a product highly similar to the interleukin 1 receptor type 1," FEBS Lett. 318(1):83-87 (1993).
Yanagisawa et al., "The expression of ST2 gene in helper T cells and the binding of ST2 protein to myeloma-derived RPMI8226 cells," J. Biochem. 121(1):95-103 (1997).
Zebrack et al., "Usefulness of high-sensitivity C-reactive protein in predicting long-term risk of death or acute myocardial infarction in patients with unstable or stable angina pectoris or acute myocardial infarction," Am. J. Cardiol. (Jan. 2002).
International Search Report for PCT/US2007/067333, mailed Jan. 23, 2008.
International Preliminary Report on Patentability for PCT/US2007/067333, issued Oct. 28, 2008.
Written Opinion of the International Searching Authority for PCT/US2007/067333, mailed Jan. 23, 2008.
Orntoft et al., "Genome-wide study of gene copy numbers, transcripts, and protein levels in pairs of non-invasive and invasive human transitional cell carcinomas," Mol. Cell.Proteomics 1:37-45 (2002).
Linares et al., Rheumatology 5:66-69 (1986)(Abstract).
Supplementary European Search Report for EP07761219, completed Apr. 9, 2009.
Partial European Search Report for EP 11177461, completed Sep. 12, 2011.
European Search Report for EP 10171764, completed Sep. 24, 2010.
Kip et al., "The problem with composite end points in cardiovascular studies," J. Am. Coll. Cardiol. 51:701-707 (2008).
Ordonez-Llamos et al., "A formula for combining ST2 and NT-pro-BNP enhances prognostic accuracy in patients with heart failure," Clin. Chem. 54:A99, (2008).
Tung et al., "Amino-terminal pro-brain natriuretic peptide for the diagnosis of acute heart failure in patients with previous obstructive airway disease," Annals. Emerg. Med. 48:66-74, (2006).
U.S. Appl. No. 14/290,465, filed May 29, 2014, Lee.
U.S. Appl. No. 14/244,526, filed Apr. 3, 2014, Snider et al.
Amendment in Reply to Office Action filed in U.S. Appl. No. 13/179,173 on Nov. 15, 2011.
Amendment in Reply to Office Action filed in U.S. Appl. No. 13/179,173 on Jul. 18, 2012.
Amendment in Reply to Office Action filed in U.S. Appl. No. 13/179,173 on Feb. 11, 2013.
Amendment in Reply to Office Action filed in U.S. Appl. No. 13/179,173 on Jul. 1, 2013.
Aukrust et la., "Cytokine network in Congestive Heart Failure Secondary to Ischemic or Idiopathic Dilated Cardiomyopathy", Am. J. Cardiol., 83*3):376-382 (1999).
Chan et al., "Human IL018 Receptor and ST2L are Stable and Selective Markers for the Respective Type I and Type 2 Circulating Lymphocytes," J. Immunol 167(3) 1238-1244 (2001).
Communication issued in European Patent Application No. 11177461.8-1405 on Aug. 2, 2013.
Examination Report issued Aug. 19, 2010 in corresponding Canadian Patent Application No. 2,650,201.
Dale et al.; "Interleukin-1 receptor cluster: Gene organization of IL1R2, IL1R1, IL1RL2 (IL1-Rrp2), IL1RL1 (T1/ST2), and IL18R1 (IL-1Rrp) on human chromosome 2q." Genomics, 1999, vol. 57, p. 177-179.
EP 07761219; Apr. 9, 2009 Supplemental European Search Report.
Examiner's First Report on Patent; AU Appl. No. 2007244927; Nov. 22, 2010; 5pp.

(56) References Cited

OTHER PUBLICATIONS

First Examination Report; AU 2012202069; Jan. 17, 2014; 20 pp.
First Examination Report; AU 2013204539; Jan. 17, 2014; 20 pp.
Frangogiannis et al., "Resident Cardiac Mast Cells Degranulate and Release Preformed TNF-alpha, Initiating the Cytokine Cascade in Experimental Canine Myocardial Ischemia/Reperfusion," Circulation, 98(7): 699-710 (1998).
International Preliminary Report on Patentability for PCT/US2009/040941; issued Oct. 19, 2010.
International Search Report for PCT/US2009/040941, completed Dec. 2, 2009, mailed Dec. 3, 2009.
JP Notice of Reasons for Rejection; JP 2012-100940; Jan. 8, 2014; 15 pp.
Morrison et al.; American College of Cardiology 2002, vol. 39, pp. 202-209.
Notice of Allowance issued in U.S. Appl. No. 13/179,173 on Aug. 26, 2013.
Notice of Reasons for Rejection; JP 2009-507931; Aug. 20, 2012; 2 pp.
Notice of Reasons for Rejection; JP Appl. No. 2009-507931; Oct. 26, 2011; 3 pp.
Office Action; U.S. Appl. No. 13/179,173; Jan. 19, 2012; 21 pp.
Office Action; U.S. Appl. No. 13/179,173; Mar. 1, 2013; 8 pp.
Office Action; U.S. Appl. No. 13/179,173; Oct. 26, 2012; 10 pp.
Office Action; U.S. Appl. No. 13/179,173; Sep. 23, 2011; 8 pp.
Office Action; U.S. Appl. No. 13/787,975; Dec. 30, 2013.
Office Action; U.S. Appl. No. 13/788,922; Dec. 11, 2013.
Prosecution File History for U.S. Appl. No. 11/789,169 downloaded from U.S. Patent and Trademark Office website on Jul. 1, 2013.
Prosecution File History for U.S. Appl. No. 12/425,956 downloaded from U.S. Patent and Trademark Office website on Jul. 1, 2013.
Prosecution File History for U.S. Appl. No. 13/151,012 downloaded from U.S. Patent and Trademark Office website on Jul. 1, 2013.
Prosecution File History for U.S. Appl. No. 13/299,612 downloaded from U.S. Patent and Trademark Office website on Jul. 1, 2013.
Prosecution File History for U.S. Appl. No. 13/422,574 downloaded from U.S. Patent and Trademark Office website on Jul. 1, 2013.
Requisition by the Examiner to Avoid Abandonment; CA 2,650,201; Dec. 15, 2011; 3 pp.
Requisition by the Examiner to Avoid Abandonment; CA 2,484,897; Feb. 4, 2014; 2 pp.
Ridker et al., England J. Medicine 2000, vol. 324, pp. 836-843.
Second Office Action; CN 201110387886.6; Feb. 19, 2014; 13 pp.
Supplementary European Search Report and Search Opinion for European Application No. EP 09731842, search and opinion mailed Apr. 1, 2011, search completed Feb. 28, 2011.
Sutton et al., "Left Ventricular Remodeling after Myocardial Infarction: Pathophysiology and Therapy", Circulation; Jun. 27, 2000; 101(25):2981-8.
Tominaga et al., The Existence of a Growth-Specific DNA Binding Factor for the Promoter Region of Mouse ST2 Gene; FEBS Lett. Nov. 14, 1994; 354(3):311-4.
Written Opinion of the International Searching Authority for PCT/US2009/040941, completed Dec. 2, 2009, mailed Dec. 3, 2009.
European Search Report; EP 14 18 8319; Feb. 13, 2015; 8 pp.
Australian Office Action; AU Appl. No. 2012202069; Jul. 10, 2015; 13 pp.

\* cited by examiner

Subjects Diagnosed with Heart Failure

Subjects Not Diagnosed with Heart Failure

FIGURE 12A
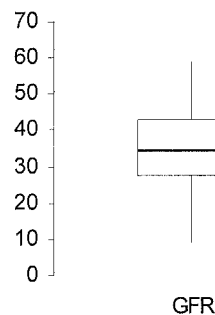
FIGURE 12B
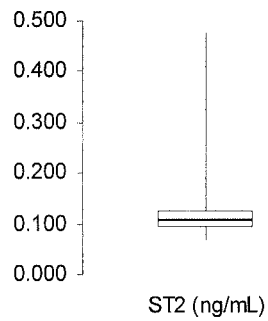
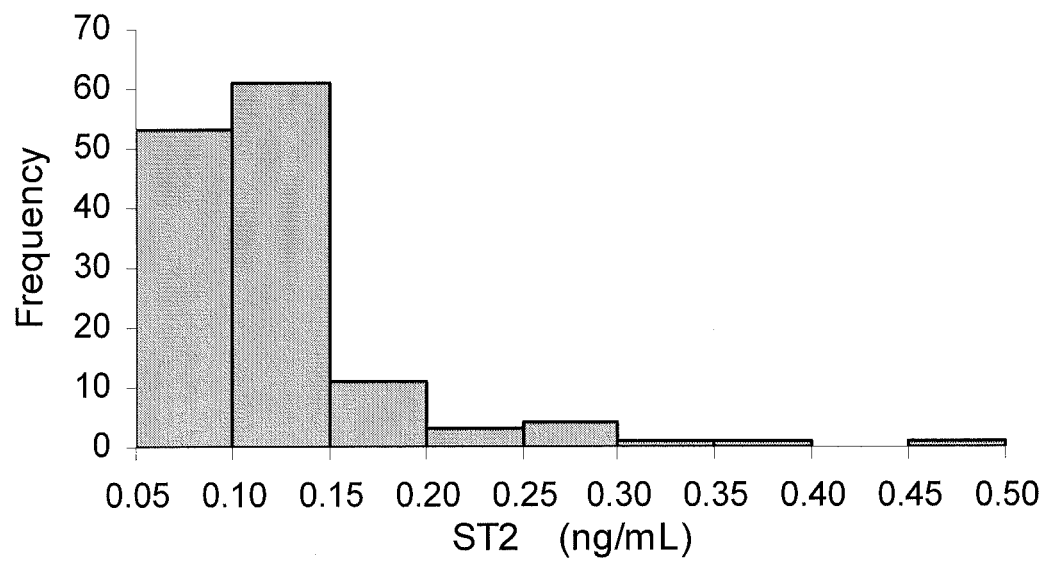
FIGURE 13

METHODS OF IDENTIFYING A SUBJECT AS HAVING HEART FAILURE

CLAIM OF PRIORITY

This application is a continuation application of U.S. patent application Ser. No. 13/179,173 (issued as U.S. Pat. No. 8,617,825), filed on Jul. 8, 2011, which is a continuation application of U.S. patent application Ser. No. 11/789,169 (issued as U.S. Pat. No. 7,998,683), filed on Apr. 24, 2007, which claims the benefit of U.S. Provisional Patent Application Ser. No. 60/794,354, filed on Apr. 24, 2006, U.S. Provisional Patent Application Ser. No. 60/800,362, filed on May 15, 2006, and U.S. Provisional Patent Application Ser. No. 60/904,608, filed on Mar. 2, 2007. The entire contents of each of the foregoing applications are hereby incorporated by reference.

FIELD OF THE INVENTION

The invention relates to methods for predicting mortality and detecting the presence of severe disease by measuring circulating levels of ST2 and/or IL-33, alone or in combination with other biomarkers.

BACKGROUND

Clinical evaluation of subjects, particularly those with non-specific symptoms such as chest pain or discomfort, shortness of breath, nausea, vomiting, eructation, sweating, palpitations, lightheadedness, fatigue, or fainting, can present significant challenges, as the cause and severity of the subject's condition may not always be apparent. The decision whether to treat a subject aggressively or conservatively, or to admit the subject as an inpatient or to send them home, may sometimes be made solely on a physician's clinical assessment or "gut feeling" as to the individual's actual condition. Biomarkers that indicate a subject's likelihood of an adverse outcome, e.g., mortality, and/or the presence of severe disease, would significantly enhance the physician's ability to make informed treatment decisions.

SUMMARY

The present invention is based, at least in part, on the discovery that serum levels of the biomarker ST2 (Growth Stimulation-Expressed Gene 2, also known as Interleukin 1 Receptor Like 1 (IL1RL-1)) can be used to predict clinical outcome, e.g., death, within a specific time period, e.g., 30 days, 3 or 6 months, or a year or more, or to detect the presence of severe disease, regardless of the underlying causes of symptoms or ultimate diagnosis. Changes in the level of ST2 over time, e.g., over a few days or more, can also be used to predict clinical outcome, e.g., in patients hospitalized after an acute event.

The methods described herein include measuring ST2 levels as well as monitoring changes in ST2 levels over time (e.g., ratios) to provide diagnostic and prognostic evaluation of patients, e.g., patients with non-specific symptoms, e.g., acutely dyspneic patients and those with chest pain.

IL-33 has been identified as the ligand for ST2. Thus, the invention includes methods for evaluating patients by monitoring biomarker levels of ST2 and/or IL-33 levels, as well as ST2/IL-33 complexes, and ratios of ST2:IL-33 complexes to free ST2 and/or IL-33.

In addition, the methods can include using additional diagnostic methods, including evaluating organ function and/or levels of adjunct biomarkers such as troponin (Tn, e.g., TnI or TnT), brain natriuretic peptide (BNP), proBNP, NT-proBNP, atrial natriuretic peptide (ANP), NT-proANP, proANP, C-reactive peptide (CRP), Blood Urea Nitrogen (BUN), D-dimers (degradation products of cross-linked fibrin, whose level becomes elevated following clot formation), albumin, liver function enzymes, measures of renal function (e.g., creatinine, creatinine clearance rate, or glomerular filtration rate) and/or bacterial endotoxin. In some embodiments, the methods include measuring ST2 and/or a change in ST2 levels over time in addition to BUN, NT-proBNP or BNP, and/or TnI.

Thus, in one aspect, the invention features methods for evaluating the risk of death or readmission within a specific time period, e.g., 30, 60, 90, or 180 days (e.g., one, two, three, or six months), or one, two, or five years, for a subject. The methods include obtaining a sample, e.g., blood, serum, plasma, urine, or body tissue from the subject; determining a biomarker level of ST2 and/or IL-33 in the sample; and comparing the biomarker level of ST2 and/or IL-33 in the sample to a reference level of ST2 and/or IL-33. A comparison of the biomarker level of ST2 and/or IL-33 in the sample versus the reference indicates the subject's risk of death or readmission within the specific time period. In some embodiments, the specific time period is one year.

In some embodiments, the reference level represents a level in a subject or group of subjects who have a low risk of death within one year. In some embodiments, e.g., wherein the biomarker level of ST2 is measured using an immunoassay, e.g., an enzyme-linked immunosorbant assay (ELISA), e.g., as described in Example 1, the reference level of ST2 is between about 0.2 and 0.3 ng/ml of serum, e.g., the level can be 0.20, 0.23, 0.25, 0.27, or 0.29 ng/ml of serum, and a level in the sample that is greater than or equal to the reference level indicates that the subject has an elevated, i.e., statistically significantly elevated, risk of death within one year. If an analytical technique other than the ELISA described in Example 1 is employed, the reference ST2 level may be different than described herein. However, the specific numbers recited herein should be construed to be equivalent to corresponding numbers generated using other analytical techniques. In some embodiments, the elevated risk of death is at least 20% higher, e.g., 30%, 40%, or 50% higher.

In another aspect, the invention features methods for determining the severity of one or more diseases, e.g., the present severity of diseases, in a subject. The methods include obtaining a sample from the subject; determining a biomarker level of ST2 and/or IL-33 in the sample; and comparing the biomarker level of ST2 and/or IL-33 in the sample to a reference level of ST2 and/or IL-33. The biomarker level of ST2 and/or IL-33 in the sample as compared to the reference indicates whether the one or more diseases the subject has are severe, e.g., life-threatening.

In a further aspect, the invention includes methods for monitoring a subject's condition, e.g., for deciding whether a subject has improved, e.g., improved sufficiently to be discharged from the hospital. The methods include determining a first biomarker level of ST2 and/or IL-33 in the subject, e.g., a baseline level; and determining at least one subsequent biomarker level of ST2 and/or IL-33 in the subject, e.g., a treatment level. Then, the first level and the subsequent levels are compared. If the biomarker level of ST2 and/or IL-33 decreases sufficiently, e.g., statistically significantly, or by at least 5%, 10%, 15%, 20%, or more, from the first to the subsequent levels, then the subject's condition is likely to be improving and, if either one or both levels are low enough, e.g., below a selected threshold, then the subject can be discharged, e.g., for outpatient treatment.

In some embodiments, the methods include determining a level of ST2 that indicates a subject's risk, and optionally selecting or modifying a treatment for the subject, based on a ratio of a first ST2 level, e.g., a baseline level, to a second ST2 level, e.g., a level taken some time later, e.g., one, two, three, four, or more days later. For example, if the second level of ST2 is more than a selected percentage of the first level, then the subject has a high risk and should be treated more aggressively; if the subject is already being treated, then the subject is not responding favorably to the current treatment and a new treatment should be selected, i.e., an alternate treatment to which the patient may respond more favorably. As one example, if the second level is about 85% or more of the first level (i.e., has decreased by about 15% or less), then the subject is not improving and still has a high risk of death.

In some embodiments, the level of ST2 in a subject is compared to a reference level that represents a level in a subject who does not have severe disease, e.g., has no disease or has no acute, severe disease, e.g., when measured using an ELISA, e.g., as described herein. The reference level of ST2 can be between about 0.2 and 0.3 ng/ml, e.g., the level can be about 0.20, 0.23, 0.25, 0.27, or 0.29 ng/ml of serum or plasma (as noted above, the thresholds recited herein apply when using an ELISA method as described herein; other corresponding threshold numbers can be considered as equivalent to these numbers when determined using a different method). A level in the sample that is greater than or equal to the reference level indicates that the subject has one or more severe diseases, e.g., present diseases.

In some embodiments, the reference level represents a subject with a certain prognosis. For example, when the level of ST2 is measured using an ELISA, e.g., as described herein in Example 1, the reference level can be used to determine prognosis as follows: an ST2 less than about 0.2 or 0.3 ng/ml indicates that the subject has a good prognosis, e.g., is likely to recover; an ST2 of from about 0.2 or 0.3 ng/ml to 0.7 ng/ml (or an equivalent thereof) indicates that the subject has a poor prognosis, e.g., is less likely to recover. Finally, an ST2 of greater than 0.7 ng/ml indicates a very poor prognosis, e.g., the subject is not likely to recover. In this embodiment poor prognosis would indicate that the patient is at a high risk of death or developing more severe disease within one year possibly requiring hospital admission. Very poor prognosis indicates that the patient has a high probability of death or developing more severe disease within 90 days possibly requiring hospital admission. In one study patients with an ST2 level higher than 0.7 ng/ml had a mortality rate of over 30%.

In some embodiments, the subject exhibits one or more non-specific symptoms, e.g., chest pain or discomfort, shortness of breath (dyspnea), nausea, vomiting, eructation, sweating, palpitations, lightheadedness, fatigue, and fainting. In some embodiments, the symptom is dyspnea or chest pain.

In some embodiments, the subject does not have a cardiovascular disorder. In various embodiments, the subject has a pulmonary disorder, e.g., acute infection (e.g., pneumonia), chronic obstructive pulmonary disease (COPD), and pulmonary embolism.

In certain embodiments, the subject has a liver disorder, e.g., a liver disorder associated with chemotherapy, alcohol toxicity, or drug toxicity as determined by standard liver function laboratory tests.

In some embodiments, the methods further include determining the level of an adjunct (non-ST2, non-IL-33) biomarker, e.g., Troponin, NT-proBNP, BNP, proBNP, NT-proANP, proANP, ANP, CRP, D-dimers, BUN, albumin, liver function enzymes, measures of renal function, e.g., creatinine, creatinine clearance rate, or glomerular filtration rate, and/or bacterial endotoxin, in the sample; and comparing the level of the adjunct biomarker in the sample to a reference level of the adjunct biomarker. The level of the adjunct biomarker in the sample as compared to the reference, in combination with the level of ST2 in the sample as compared to an ST2 reference level, indicates whether the subject has an elevated risk of death within a specific time period, and/or has a present severe disease. In some embodiments, the methods include determining a change in levels over time (e.g., a ratio) for the adjunct biomarker, by comparing a first level, e.g., a baseline level, to a second level, e.g., a level taken some time later, e.g., one, two, three, four, or more days later. In embodiments where a ratio of ST2 is calculated, a ratio of an adjunct biomarker can also be calculated, e.g., based on the same time period as the ratio of ST2.

In some embodiments, the subject has a BMI of 25-29, a BMI of ≥30, or renal insufficiency, e.g., the subject is selected on the basis that they have a BMI of 25-29, a BMI of ≥30, or renal insufficiency.

In some embodiments, the methods include determining a level of ST2 and a level of IL-33 in the sample; determining a ratio of ST2:IL-33 in the sample; and comparing the ratio of ST2:IL-33 to a reference ratio. The ratio of ST2:IL-33 in the sample as compared to the reference ratio indicates whether the subject has an elevated risk of death within a specific time period, and/or has present severe disease.

In another aspect, the invention provides methods for evaluating the risk of death within a specific time period, e.g., 30, 60, 90, or 180 days (6 months), or one, two, or five years, e.g., for a subject who exhibits one or more non-specific symptoms. The methods include obtaining a sample from the subject; determining a biomarker level of ST2 and/or IL-33 in the sample, and optionally a level of NT-proBNP, proBNP, or BNP in the sample; and comparing the level of ST2 and/or IL-33 in the sample, and the level of NT-proBNP in the sample (if determined), to corresponding reference levels. The level of ST2 and/or IL-33 in the sample, and the level of NT-proBNP, proBNP, or BNP in the sample, as compared to the respective reference levels indicate the subject's risk of death within the specific time period.

In some embodiments, the methods include determining levels of (i) NT-proBNP, proBNP, or BNP and (ii) ST2 in the sample. In some embodiments, the subject's risk of death within one year is as follows:

|  | ST2 < 0.20 ng/ml | ST2 ≥ 0.20 ng/ml |
|---|---|---|
| NT-proBNP < 986 pg/ml | Lowest Risk | Medium Risk |
| NT-proBNP ≥ 986 pg/ml | Medium Risk | Highest Risk |

In certain embodiments, if the subject has the highest level of risk of death or hospital readmission, the subject is treated aggressively.

In a further aspect, the invention includes methods for monitoring a subject's condition, e.g., for deciding whether a subject has improved, e.g., improved sufficiently to discharge the subject from the hospital. The methods include determining a first level of (i) a non-ST2 biomarker, e.g., NT-proBNP, proBNP, or BNP and (ii) ST2 and/or IL-33 in the subject, e.g., a baseline level; and determining at least one subsequent level of (i) the non-ST2 biomarker, e.g., NT-proBNP, proBNP, or BNP and (ii) ST2 and/or IL-33 in the subject, e.g., a treatment level. Then, the first level and the subsequent levels are compared. If the level of ST2 and/or IL-33 decreases from the first to the subsequent levels, then the subject is likely to be improving and, if the level is low enough, then the subject has improved, e.g., improved sufficiently to be discharged, e.g., for outpatient treatment. In some embodiments, the methods include determining at least a first, second, and third level of (i) a non-ST2 biomarker, e.g., NT-proBNP, proBNP, or BNP and (ii) ST2 and/or IL-33 in the subject, and comparing the levels. A difference between the levels indicates whether the subject has improved sufficiently to be discharged. Thus, for example, a decision to discharge or continue to treat on an inpatient basis can be made as follows:

|  | ST2 > threshold | ST2 < threshold |
| --- | --- | --- |
| BNP > threshold | Prognosis very poor, requires intensive treatment, do not discharge | Patient may still need treatment, favorable prognosis, possibly discharge as outpatient |
| BNP < threshold | Prognosis poor, patient may have complicating illness, if discharge monitor closely | Prognosis good |

In some embodiments, the threshold for ST2 is 0.2 ng/ml, and the threshold for BNP is 986 pg/ml.

Also provided herein are kits including one or more antibodies that bind specifically to ST2 and/or one or more antibodies that bind specifically to IL-33, and instructions for performing one or more of the methods described herein.

In a further aspect, the invention provides methods for evaluating a subject's condition. The methods include obtaining a sample from the subject; determining a biomarker level of ST2 and/or IL-33 in the sample, and determining presence or a level of one or more, e.g., all, of the following other biomarkers:
 (i) NT-proBNP, proBNP, or BNP; (ii) NT-proANP, proANP, or ANP; (iii) cardiac troponin (cTn), e.g., cTnI; (iv) D-dimers; (v) C-reactive protein (CRP); (vi) creatinine, creatinine clearance rate, or glomerular filtration rate; (vii) Blood Urea Nitrogen (BUN); (viii) bacterial endotoxin; (ix) one or more liver function enzymes; and
comparing the level of ST2 and/or IL-33 in the sample, and the level of the one or more other biomarkers in the sample, to corresponding reference levels. The level of ST2 and/or IL-33 in the sample, and the level of the other biomarker in the sample, as compared to the reference levels indicate the severity of the subject's condition.

In some embodiments, the methods described herein include measuring levels or ratios of ST2 and/or IL-33 in combination with BNP or NT-proBNP; with troponin, e.g., TnI or TnT; or with a measure of renal function, e.g., creatinine, creatinine clearance rate, or glomerular filtration rate.

In another aspect, the invention includes methods for evaluating the efficacy of a treatment in a subject. The methods include determining a first (e.g., baseline) level of circulating ST2 and/or IL-33 in a subject; comparing the first level of circulating ST2 and/or IL-33 in the subject to a predetermined reference level; selecting the subject if the first level of ST2 is above the predetermined reference level; administering a treatment to the subject; determining a second level of circulating ST2 and/or IL-33 in a subject; and comparing the first and second levels of circulating ST2 and/or IL-33. A difference between the first and second levels of circulating ST2 and/or IL-33 indicates the efficacy of the treatment in the subject. For example, a second level of circulating ST2 and/or IL-33 that is lower than the first level indicates that the treatment is effective.

As used herein, a "sample" includes any bodily fluid or tissue, e.g., one or more of blood, serum, plasma, urine, and body tissue. In certain embodiments, a sample is a serum, plasma, or blood sample.

An antibody that "binds specifically to" an antigen, binds preferentially to the antigen in a sample containing other proteins.

The methods and kits described herein have a number of advantages. For example, the methods can be used to determine whether a patient should be admitted or held as an inpatient for further assessment, regardless of whether a definitive diagnosis has been made. For example, the methods can be used for risk stratification of a given subject, e.g., to make decisions regarding the level of aggressiveness of treatment that is appropriate for the subject, based on their ST2 levels. Better treatment decisions can lead to reduced morbidity and mortality, and better allocation of scarce health care resources. The methods described herein can be used to make general assessments as to whether a patient should be further tested to determine a specific diagnosis. The methods described herein can also be used for patient population risk stratification, e.g., to provide information about clinical performance or expected response to a therapeutic intervention. The methods described herein can be used regardless of the underlying cause or ultimate diagnosis, and therefore are not limited to specific indications.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 12A-B are box graphs illustrating mean Glomerular Filtration Rate (GFR, 12A) and ST2 levels (12B) in a population of 133 subjects with moderate to severe renal insufficiency.

FIG. 13 is a bar graph illustrating the distribution of ST2 levels in the population described in Example 8.

DETAILED DESCRIPTION

Figure 1:
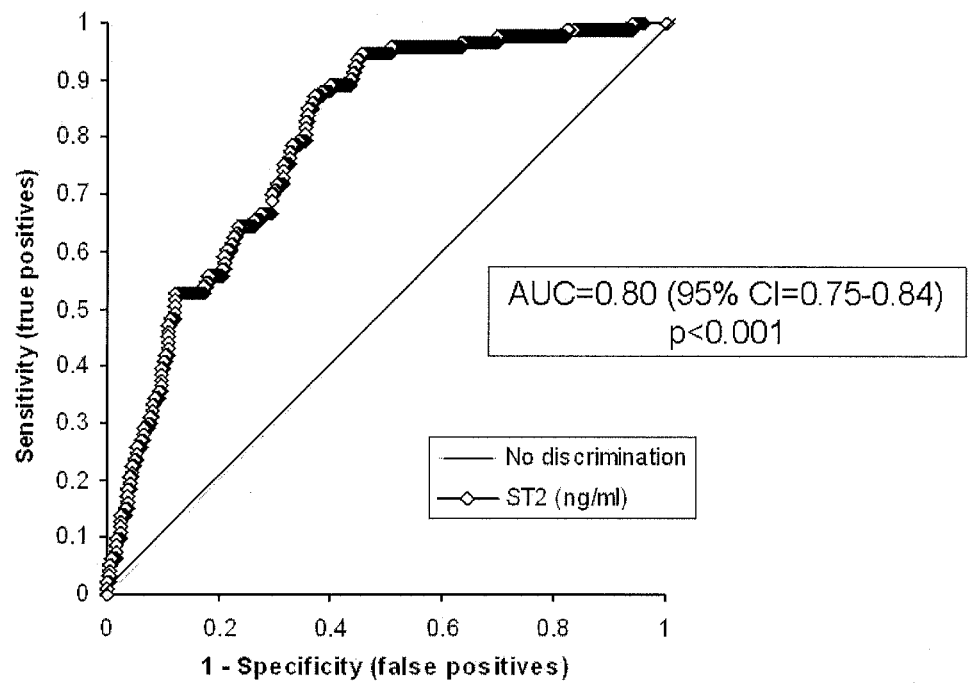
FIG. 1 is a graph illustrating receiver operating characteristic analysis for ST2 and death within one year. ST2 was useful for this purpose, as indicated by the high area under the curve (AUC).

Clinical evaluation of patients, particularly patients with non-specific symptoms such as dyspnea or chest pain, is often challenging. The results described herein provide evidence that ST2 is useful in the prognostic evaluation of patients, regardless of the underlying cause of their disease. ST2 is a powerful indicator of severe disease and imminent death, as demonstrated herein in several completely different populations with completely different symptoms (see Examples 1-6).

Predicting Mortality

Elevated concentrations of ST2 are markedly prognostic for death within one year, with a dramatic divergence in survival curves for those with elevated ST2 soon after presentation, regardless of the underlying diagnosis. As one example, there is a dramatic relationship between elevations of ST2 and the risk for mortality within one year following presentation with dyspnea. The relationship between ST2 and death in dyspneic patients was independent of diagnosis, and superseded all other biomarker predictors of mortality in this setting, including other markers of inflammation, myonecrosis, renal dysfunction, and most notably NT-proBNP, a marker recently described as having value for predicting death in this population (Januzzi et al., Arch. Intern. Med. 2006; 166(3):315-20). Indeed, most of the mortality in the study was concentrated among subjects with elevated ST2 levels at presentation; however, the combination of an elevated ST2 and NT-proBNP was associated with the highest rates of death within one year.

Such a multi-marker approach for risk stratification has been proposed for patients with acute coronary syndromes (Sabatine et al., Circulation 2002; 105(15):1760-3), but no such strategy has yet been proposed for the evaluation for the patient with non-specific symptoms such as undifferentiated dyspnea or general complaint of chest pain.

Determining Severity of Disease

Elevated concentrations of ST2 are correlated with the presence of severe disease in a subject, regardless of the underlying cause of the disease. As one example, in a population of patients presenting with chest pain, the highest levels of disease were associated with severe disease including chronic obstructive pulmonary disease (COPD), lymphoma, sepsis, alcohol abuse, and pulmonary embolism (see Example 5).

Therefore, for undiagnosed subjects, the methods described herein can be used to determine how aggressively a diagnosis should be sought; a high ST2 level would indicate the presence of severe disease, and suggest that the subject should be treated as a high-risk case. For subjects with a known diagnosis, the methods described herein can be used to help determine the severity of the underlying pathology; again, a higher ST2 level is associated with more severe disease.

General Methodology

In general, the methods described herein include evaluating circulating levels (e.g., levels in blood, serum, plasma, urine, or body tissue) of ST2 and/or IL-33 in a subject, e.g., a mammal, e.g., a human. These levels provide information regarding the subject's likelihood of experiencing an adverse outcome, e.g., mortality, e.g., within a specific time period, e.g., 30 days, 60 days, 90 days, 6 months, one year, two years, three years, or five years. These levels also provide information regarding the severity of disease in the subject. In some embodiments, the level of ST2 and/or IL-33 is determined once, e.g., at presentation. In some embodiments, the level of ST2 and/or IL-33 is determined 2, 4, 6, 8, 12, 18, and/or 24 hours, and/or 1-7 days after the onset of symptoms. Where more than one level is determined, a ratio of ST2 can be calculated that quantifies whether and how much the level of ST2 in the subject has increased or decreased.

In some embodiments, the level of ST2 and/or IL-33 is determined more than once; in that case, the higher measurement, or the most recent measurement, can be used. In embodiments where the level of ST2 and/or IL-33 is determined more that once, the highest level can be used, or the difference between the levels (i.e., the magnitude and direction of the difference) can be determined and used. Thus, a ratio of ST2 can be determined that represents the change (e.g., the magnitude and direction, e.g., increase or decrease) in ST2 levels over time, e.g., over the course of a few days, e.g., 3 days or more, or over the course of weeks or months; the ratio is indicative of the subject's risk level and the presence of severe disease. Levels of ST2 and/or IL-33 can also be determined multiple times to evaluate a subject's response to a treatment. For example, a biomarker level of ST2 and/or IL-33 taken after administration of a treatment, e.g., one or more doses or rounds of a treatment, can be compared to levels of ST2 and/or IL-33 before the treatment was initiated. The difference between the ST2 levels would indicate whether the treatment was effective; e.g., a reduction in ST2 levels would indicate that the treatment was effective. The difference between the ST2 levels can also be used to monitor a subject's condition, e.g., to determine if the subject is improving, e.g., improving enough to be discharged from a hospital, to be treated less aggressively, or to be followed up at greater time intervals.

Evaluating circulating levels of ST2 and/or IL-33 in a subject typically includes obtaining a biological sample, e.g., serum, plasma or blood, from the subject. Levels of ST2 and/or IL-33 in the sample can be determined by measuring levels of polypeptide in the sample, using methods known in the art and/or described herein, e.g., immunoassays such as enzyme-linked immunosorbant assays (ELISA). Alternatively, levels of ST2 and/or IL-33 mRNA can be measured, again using methods known in the art and/or described herein, e.g., by quantitative PCR or Northern blotting analysis.

Once a level or ratio of ST2 and/or IL-33 has been determined, the level or ratio can be compared to a reference level or ratio. In some embodiments, e.g., where the level of ST2 is determined using an ELISA, e.g., as described in Example 1, the reference level will represent a threshold level, above which the subject has an increased risk of death, and/or has a severe disease. The reference level chosen may depend on the methodology used to measure the levels of ST2. For example, in some embodiments, where circulating levels of soluble ST2 are determined using an immunoassay, e.g., as described herein, the reference level is about 0.20, 0.23, or 0.29 ng/ml of serum, and a level of ST2 above that reference level indicates that the subject has an increased risk of death, and/or has a severe disease.

Where a ratio has been determined, e.g., using a first and second measurement of ST2, the reference ratio will represent an amount and direction of change that indicates whether the subject has an increased risk of death and/or has a severe disease. As one example, an ST2 ratio can be calculated based on a first measurement, e.g., a baseline measurement taken when a subject presents for treatment, e.g., to an ED, and a second measurement, e.g., a measurement taken about three to four days later. If the ratio of first and second ST2 levels over time is about 0.85 or higher, i.e., the ST2 levels have decreased less than about 15% (or have stayed the same or increased), then the subject has a very high risk of imminent death. Ratios below about 0.85 (where the ST2 levels have decreased more than about 15%) indicate that the subject has a lower risk of imminent death.

This information allows a treating physician to make more accurate treatment decisions; for example, when the results of the determination indicate that the subject has a level equal to or above a reference level, e.g., above about 0.20 ng/ml, 0.23 ng/ml, or 0.29 ng/ml of serum, or a ratio above a reference ratio, the subject may be admitted to the hospital as an inpatient, e.g., in an acute or critical care department. In some embodiments, comparison of ST2 to a reference level or ratio can be used to determine a subject's prognosis. For example, when the level of ST2 is measured using an ELISA, e.g., as described herein in Example 1, the reference level can be used to determine prognosis as follows: an ST2< about 0.20 ng/ml or 0.23 ng/ml indicates that the subject has a good prognosis, e.g., is likely to recover; an ST2 of from about 0.20 ng/ml or 0.23 ng/ml to about 0.7 ng/ml indicates that the subject has a poor prognosis, e.g., is less likely to recover. Finally, an ST2 of greater than about 0.7 ng/ml indicates a very poor prognosis, e.g., the subject is not likely to recover. As another example, a ratio of first and second ST2 levels over time above about 0.85 indicates a poor prognosis, while a ratio of about 0.85 of below indicates a good prognosis.

Additional testing may be performed, to determine the subject's actual condition. More aggressive treatment may be administered either before or after additional testing. For example, in the case of a suspected MI the subject may be sent for more extensive imaging studies and/or cardiac catheterization.

In some embodiments, both levels of ST2 and IL-33 are determined, and the information from the comparison of both biomarkers with their respective reference levels provides cumulative information regarding an increased risk of death, and/or presence of a severe disease in the subject. In some embodiments, the ratio of ST2 to IL-33 may be determined, and the ratio compared to a reference ratio that represents a threshold ratio above which the subject has an increased risk of death, and/or has a severe disease. In some embodiments, the presence of IL-33/ST2 complexes is detected, and the level of such complexes is indicative of risk of death and/or the presence of severe disease.

In some embodiments, the methods include the use of additional diagnostic methods to identify underlying pathology. Any diagnostic methods known in the art can be used, and one of skill in the art will be able to select diagnostic methods that are appropriate for the subject's symptoms. In some embodiments, the methods described herein include other diagnostic methods in addition to or as an alternative to the measurement of other biomarkers, e.g., physical measurements of lung function or cardiac function as are known in the art.

For example, the methods described herein include measuring levels of ST2 and/or IL-33 and one or more additional biomarkers that aid in the subject's diagnosis. As one example, for a subject who has chest pain or dyspnea, biomarkers indicative of cardiac disease can be measured, e.g., cardiac troponin (cTn), e.g., cTnI, BNP, and/or ANP; alternatively or in addition, biomarkers of pulmonary disease can be measured, e.g., D-dimers for pulmonary embolism. Thus, in subjects presenting with symptoms that include MI in their differential diagnoses, the methods can include measuring levels of, cTnI, BNP or NTproBNP or proBNP in addition to ST2 and/or IL-33, to determine whether the subject is having an MI. In subjects presenting with symptoms that include heart failure (HF) in their differential diagnoses, the methods can include measuring levels of BNP or NTproBNP or proBNP in addition to ST2 and/or IL-33, to determine whether the subject is having HF. In subjects presenting with symptoms that include COPD in their differential diagnoses, the methods can include measuring lung function in addition to levels of ST2 and/or IL-33, to determine whether the subject has COPD. One of skill in the art will appreciate that there are a number of additional diagnostic methods that can be applied, depending on the situation and the subject's condition. In some embodiments, the methods include measuring levels of BUN, and the presence of elevated BUN and elevated ST2 places the subject in the highest risk category.

ST2

The ST2 gene is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The trans-membrane form of ST2 is thought to play a role in modulating responses of T helper type 2 cells (Lohning et al., Proc. Natl. Acad. Sci. U.S.A. 95(12):6930-5 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2, which is a soluble secreted form; and ST2L, a transmembrane receptor form that is very similar to the interleukin-1 receptors. The HUGO Nomenclature Committee designated the human homolog, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured.

Methods for detecting and measuring ST2 are known in the art, e.g., as described in U.S. Pat. Pub. Nos. 2003/0124624, 2004/0048286 and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

In some embodiments, the methods include determining the identity of the nucleotide sequence at RefSNP ID: rs1041973.

IL-33

IL-33 was recently identified as the ligand for ST2, and the presence of increased levels of IL-33 in various inflammatory disorders has been described (see Schmitz et al., Immunity 23(5):479-90 (2005); U.S. Pat. Pub. No. 2005/0203046). In the methods described herein, IL-33 can be measured instead of or in addition to ST2. The ratio of ST2 to IL-33 can also be determined.

The nucleic acid sequence of IL-33 can be found at GenBank Acc. No. NM_033439.2, and the polypeptide sequence is at GenBank Acc. No. NP_254274.1. Additional information is available in the public databases at Gene ID: 90865, MIM ID #*608678, and UniGene No. Hs.348390. IL-33 is also known as Chromosome 9 Open Reading Frame 26 (C9ORF26); Nuclear Factor from High Endothelial Venules (NFHEV); and Interleukin 33. See also Baekkevold et al., Am. J. Path. 163: 69-79 (2003).

Methods for measuring levels of IL-33 are known in the art, see, e.g., Schmitz et al., Immunity. 23(5):479-90 (2005), and U.S. Pat. Pub. No. 2005/0203046.

Other Biomarkers

The methods described herein can also include measuring levels of other biomarkers in addition to ST2 and/or IL-33. Suitable biomarkers include proBNP, NT-proBNP, BNP, NT-proANP, proANP, ANP, troponin, CRP, IL-6, D-dimers, BUN, liver function enzymes, albumin, measures of renal function, e.g., creatinine, creatinine clearance rate, or glomerular filtration rate, and/or bacterial endotoxin. Methods for measuring these biomarkers are known in the art, see, e.g., U.S. Pat. Pub. Nos. 2004/0048286 and 2005/0130136 to Lee et al.; Dhalla et al., Mol. Cell. Biochem. 87:85-92 (1989); Moe et al., Am. Heart. J. 139:587-95 (2000); Januzzi et al., Eur. Heart J. 27(3):330-7 (2006); Maisel et al., J. Am. Coll. Cardiol. 44(6):1328-33 (2004); and Maisel et al., N. Engl. J. Med. 347(3):161-7 (2002), the entire contents of which are incorporated herein by reference. Liver function enzymes include alanine transaminase (ALT); aspartate transaminase (AST); alkaline phosphatase (ALP); and total bilirubin (TBIL).

In these embodiments, levels of ST2 and/or IL-33 and one or more additional biomarkers are determined, and the information from the comparison of the biomarkers with their respective reference levels provides additional information regarding the subject's risk of death and/or the presence of a severe disease in the subject, which may provide more accurate and specific information regarding the subject's risk. The levels can then be compared to a reference ratio that represents a threshold ratio above which the subject has an increased risk of death, and/or has a severe disease.

As one example, the methods can include determining levels of NT-proBNP and ST2. The levels indicate the subject's risk of death, e.g., as shown in Table 1A.

TABLE 1A

Risk of Death Based on Circulating Levels of NT-proBNP and ST2

|  | ST2 < 0.20 ng/ml | ST2 ≥ 0.20 ng/ml |
| --- | --- | --- |
| NT-proBNP < 986 pg/ml | Lowest Risk | Medium Risk |
| NT-proBNP ≥ 986 pg/ml | Medium Risk | Highest Risk |

As shown in Table 1A, the lowest risk of death, e.g., no greater risk of death than in normal patients or healthy individuals, occurs when both ST2 and NT-proBNP levels are low, and the highest risk of death, i.e., a statistically significantly increased risk, e.g., greater than 20% increased risk of death, e.g., a greater than 30, 40, or 50% higher risk than a normal patient or healthy individual, occurs when both ST2 and NT-proBNP levels are high.

As another example, the methods can include determining levels of ST2 and BUN. The levels indicate the subject's risk of death, e.g., as shown in Table 1B.

TABLE 1B

Risk of Death Based on Circulating Levels of BUN and ST2

|  | ST2 < 0.20 ng/ml | ST2 ≥ 0.20 ng/ml |
| --- | --- | --- |
| BUN < 40 mg/dL | Lowest Risk | Medium Risk |
| BUN ≥ 40 mg/dL | Medium Risk | Highest Risk |

As shown in Table 1B, the lowest risk of death, e.g., no greater risk of death than in normal patients or healthy individuals, occurs when both ST2 and BUN levels are low, and the highest risk of death, e.g., a statistically significantly increased risk of death, e.g., a risk greater than 30, 40, or 50% higher risk than a normal patient or healthy individual, occurs when both ST2 and BUN levels are high.

Selecting a Treatment—Aggressive vs. Conservative

Once it has been determined that a subject has a circulating level of ST2 and/or IL-33 above a predetermined reference level, the information can be used in a variety of ways. For example, if the subject has elevated ST2 levels, e.g., as compared to a reference level, a decision to treat aggressively can be made, and the subject can be, e.g., admitted to a hospital for treatment as an inpatient, e.g., in an acute or critical care department. Portable test kits could allow emergency medical personnel to evaluate a subject in the field, to determine whether they should be transported to the ED. Triage decisions, e.g., in an ED or other clinical setting, can also be made based on information provided by a method described herein. Those patients with high ST2 and/or IL-33 levels can be prioritized over those with lower ST2 or IL-33 levels.

The methods described herein also provide information regarding whether a subject is improving, e.g., responding to a treatment, e.g., whether a hospitalized subject has improved sufficiently to be discharged and followed on an outpatient basis. In general, these methods will include determining the levels of ST2 and/or IL-33 in the subject multiple times. A decrease in ST2 and/or IL-33 levels over time indicates that the subject is likely to be improving. The most recent levels of ST2 and/or IL-33 can also be compared to a threshold, as described herein, to determine whether the subject has improved sufficiently to be discharged.

The subject may also be considered for inclusion in a clinical trial, e.g., of a treatment that carries a relatively high risk. The subject can be treated with a regimen that carries a relatively higher risk than would be considered appropriate for someone who had a lower risk of imminent mortality, e.g., mortality within 30 days or within 1 year of presentation.

Beyond the clinical setting, information regarding a subject's ST2 and/or IL-33 can be used in other ways, e.g., for payment decisions by third party payors, or for setting medical or life insurance premiums by insurance providers. For example, a high level of ST2 and/or IL-33, e.g., a level above a predetermined threshold level, may be used to decide to increase insurance premiums for the subject.

Patient Populations

The methods described herein are useful in a wide variety of clinical contexts. For example, the methods can be used for general population screening, including screening by doctors, e.g., in hospitals and outpatient clinics, as well as the ED. As one example, levels of ST2 and/or IL-33 can be determined at any time, and if ST2 and/or IL-33 is elevated, the physician can act appropriately.

Although the methods described herein can be used for any subject, at any time, they are particularly useful for those subjects for whom a diagnosis, or the severity of a condition, is difficult to determine. For example, such subjects may present with non-specific symptoms, e.g., symptoms that do not indicate a specific diagnosis. Non-specific symptoms include, but are not limited to, chest pain or discomfort, shortness of breath, nausea, vomiting, eructation, sweating, palpitations, lightheadedness, fatigue, and fainting. Each symptom can have varied etiology.

Chest Pain

Chest pain is the chief complaint in about 1 to 2 percent of outpatient visits, and although the cause is often noncardiac, heart disease remains the leading cause of death in the United States. Therefore, distinguishing between serious and benign causes of chest pain is crucial. The methods described herein are useful in making this determination.

A subject presenting to the ED with chest pain may have esophageal pain, an ulcer, acute lung problems such as pulmonary embolus (PE) (potentially fatal), rupturing or dissecting aneurysm (highly lethal), gall bladder attack, pericarditis (inflammation of the sack around the heart), angina pectoris (cardiac pain without damage), or an MI (potentially fatal). A precise diagnosis may be difficult to make immediately, but the decision whether to admit the subject or to treat them conservatively should generally be made immediately. If the methods described herein indicate that the subject has an increased risk of an adverse clinical outcome, e.g., imminent mortality or severe disease, then the decision can be made to treat the subject aggressively, to potentially prevent the adverse outcome.

Additional information about treatment and diagnosis of chest pain may be found, e.g., in Cayley, Am. Fam. Phys. 72(10):2012-2028 (2005).

Dyspnea

Dyspnea, or shortness of breath (also defined as abnormal or uncomfortable breathing), is a common symptom of subjects on presentation to the ED. The differential diagnosis for dyspnea includes four general categories: (1) cardiac, (2) pulmonary, (3) mixed cardiac or pulmonary, and (4) noncardiac or nonpulmonary.

Cardiac causes of dyspnea include right, left, or biventricular congestive heart failure with resultant systolic dysfunction, coronary artery disease, recent or remote myocardial infarction, cardiomyopathy, valvular dysfunction, left ventricular hypertrophy with resultant diastolic dysfunction, asymmetric septal hypertrophy, pericarditis, and arrhythmias.

Pulmonary causes include obstructive (e.g., chronic obstructive pulmonary disease (COPD) and asthma) and restrictive processes (e.g., extrapulmonary causes such as obesity, spine or chest wall deformities, and intrinsic pulmonary pathology such as interstitial fibrosis, pneumoconiosis, granulomatous disease or collagen vascular disease).

Mixed cardiac and pulmonary disorders include COPD with pulmonary hypertension and cor pulmonale, deconditioning, pulmonary emboli, and trauma.

Noncardiac or nonpulmonary disorders include metabolic conditions such as anemia, diabetic ketoacidosis and other, less common causes of metabolic acidosis, pain in the chest wall or elsewhere in the body, and neuromuscular disorders such as multiple sclerosis and muscular dystrophy. Obstructive rhinolaryngeal problems include nasal obstruction due to polyps or septal deviation, enlarged tonsils, and supraglottic or subglottic airway stricture.

Dyspnea can also present as a somatic manifestation of psychiatric disorders, e.g., an anxiety disorder, with resultant hyperventilation.

Additional information regarding the evaluation and treatment of dyspnea can be found, e.g., in Morgan and Hodge, Am. Fam. Phys. 57(4):711-718 (1998).

Special Populations

Certain populations of subjects may benefit particularly from the methods described herein. These subjects include people for whom BNP or NT-proBNP is less useful, such as in those with impaired renal function (Anwaruddin et al., J. Am. Coll. Cardiol. 47(1):91-7 (2006); McCullough et al., Am. J. Kidney Dis. 41(3):571-9 (2003)), or in those who are overweight (Body Mass Index (BMI) of 25-29) or obese (BMI≥30) (Krauser et al., Am. Heart J. 149(4):744-50

(2005); McCord et al., Arch. Intern. Med. 164(20):2247-52 (2004)). It is known and accepted in the field that patients with a high BMI usually have levels of natriuretic peptide that are lower than expected relative to a normal body mass patient for the same level of disease; the exact mechanism for this phenomenon is not known. It has been shown that circulating levels of ST2 are not influenced by BMI, therefore, the determination of ST2 levels is more useful than natriuretic peptide levels in subjects with high BMI. Thus, the methods described herein can include determining a subject's BMI, and if the subject is overweight or obese, selecting the patient for determination of ST2 and/or IL-33 levels, as described herein.

EXAMPLES

The invention is further described in the following examples, which do not limit the scope of the invention described in the claims.

Example 1

Sandwich ELISA Assay

This example uses the ST2 ELISA Kit manufactured by Medical & Biological Laboratories Co., Ltd. (MBL International Corp., Woburn, Mass.), no. 7638. This kit is a sandwich ELISA assay utilizing monoclonal antibodies for both capture and detection. This procedure is intended to analyze a full plate of samples assayed in replicates at a 1:3 dilution factor and closely follows the manufacturers' protocol. Kits should be stored at 4° C. until use. The procedure described in this example is optimized for human serum or plasma collected in citrate or EDTA anticoagulant tubes. Plasma collected in heparin anticoagulant tubes should not be used in this assay as heparin binds ST2 and inhibits measurement by this ELISA protocol. Plasma or serum samples may be used fresh or stored frozen. This assay is not adversely effected by up to 3 freeze and thaw cycles of plasma samples.

Reagents should be prepared fresh from a new kit immediately before performing the assays. Allow the kit to equilibrate to room temperature prior to use. Reagents not explicitly discussed below are provided by the manufacturer ready to use.
1. Wash solution—wash solution is provided by the manufacturer as a 10× concentrate solution. To make 1 liter of wash solution dilute 100 ml of the 10× concentrate provided with 900 ml of distilled water.
2. Detector solution—the detector solution is prepared by diluting the detector concentrate 1:101 with the detector diluent. For a full 96 well plate of samples 10 ml of detector solution is required. To prepare 10 ml of detector solution use a pipette to transfer 10 ml of the blue colored detector diluent to a 15 ml orange top polypropylene tube. Ad 100 µl of the detector concentrate to this volume of detector diluent.
    a. NOTE: this reagent should be prepared during the first assay incubation step.
3. Calibrator stock—reconstitute the calibrator protein by dissolving the lyophilized protein in the amount of distilled water defined by the manufacturer for this manufacturing lot to yield a stock solution of 8 ng/ml. This volume specification is included in the product insert.

Preparation of Standards and Samples
All of the following should be prepared in labeled 1.5 ml polypropylene tubes to be transferred to the assay plate with the P200 pipetter.
Standards
The standard curve is prepared by making 2 fold serial dilutions of the 8 ng/ml stock solution.
1. Using a P1000 pipette transfer 250 µl of Assay Diluent to 8 1.5 ml polypropylene tubes labeled S1-S8.
2. Using the same P1000 pipette transfer 250 µl of the 8 ng/ml Calibrator stock solution to tube S1. This tube is now 4 ng/ml calibrator protein.
    a. Mix thoroughly by gently pipetting 3 times being careful not to create bubbles.
3. Using the same P1000 pipette and a fresh tip for each of the following transfer 250 µl of the reagent in tube S1 to tube S2, repeat the mixing.
4. Repeat step 3 for S2 to S3, S3 to S4, S4 to S5, S5 to S6 and S6 to S7. S8 will be the reagent blank so do not transfer the calibrant protein to this well.
    a. Tubes S1-S6 and S8 will now have 250 µl of reagent and tube S7 will have 450 µl Samples
The plate is set up so that each sample is analyzed as a 1:3 dilution in duplicate.
1. Label a 1.5 ml polypropylene tube for each sample.
2. Using the P200 pipette transfer 160 µl of Assay Diluent to each tube.
3. Using a P200 pipette transfer 80 µl of serum or plasma from sample 1 to tube 1. Mix carefully by pipetting 3 times without making bubbles.
4. Continue transferring samples to the sample tubes by repeating step 2 for each sample.

Procedure
1. Use the P200 pipette transfer the standards and diluted serum samples quickly to the 96 well assay plate, as shown in Table 2.
    a. Set the P200 pipette for 100 µl
    b. Transfer 100 µl of the standard curve dilutions to each of columns 1 & 2 in the assay plate
    c. Transfer 100 µl of each of the serum samples to the assay plate in exactly the same positions as shown in the plate map below.
2. Cover the assay plate with the provided shield and incubate at room temperature for 60 minutes.
3. Using the plate autowasher wash the plate 4 times.
4. Detector: using the 8 channel multichannel pipette transfer 100 µl of the detector solution to each well and incubate at room temperature for 60 minutes.
    a. NOTE: this reagent was to be prepared during the first incubation step.
    b. NOTE: use a disposable reagent vessel for this reagent addition. ALWAYS use a fresh disposable reagent vessel for each reagent. It is not necessary to change pipette tips during this step.
5. Wash the plate as in step 3
6. Substrate: using the 8 channel multichannel pipette transfer 100 µl of the Substrate to each well and incubate at room temperature for 30 minutes.
    a. The Substrate reagent is provided ready to use by the manufacturer.
7. Stop: at the completion of the Substrate incubation using the 8 channel multichannel pipette transfer 100 µl of the Stop solution to each well.
    a. The Stop Solution reagent is provided ready to use by the manufacturer.

8. Read the plate at 450 nm with background correction at 620 nm.
    a. The plate should be read within 30 minutes after stopping the reaction.
9. Enter the absorbance readings in the provided spreadsheet for analysis.

TABLE 2

Map of Exemplary 96 Well Assay Plate

|   | 1 | 2 | 3 | 4 | 5 | 6 | 7 | 8 | 9 | 10 | 11 | 12 |
|---|---|---|---|---|---|---|---|---|---|----|----|----|
| A | 4.0    |   | 1 | 1 | 9  | 9  | 17 | 17 | 25 | 25 | 33 | 33 |
| B | 2.0    |   | 2 | 2 | 10 | 10 | 18 | 18 | 26 | 26 | 34 | 34 |
| C | 1.0    |   | 3 | 3 | 11 | 11 | 19 | 19 | 27 | 27 | 35 | 35 |
| D | 0.5    |   | 4 | 4 | 12 | 12 | 20 | 20 | 28 | 28 | 36 | 36 |
| E | 0.25   |   | 5 | 5 | 13 | 13 | 21 | 21 | 29 | 29 | 37 | 37 |
| F | 0.125  |   | 6 | 6 | 14 | 14 | 22 | 22 | 30 | 30 | 38 | 38 |
| G | 0.0625 |   | 7 | 7 | 15 | 15 | 23 | 23 | 31 | 31 | 39 | 39 |
| H | 0.0    |   | 8 | 8 | 16 | 16 | 24 | 24 | 32 | 32 | 40 | 40 |

Table 2 is a map of an exemplary 96 well assay plate, with control reactions in column 1, and each sample 1-40 analyzed in duplicate in columns 3-12.

Example 2

Measurement of Soluble ST2 Concentrations for the Evaluation of Patients with Acute Dyspnea In this example, the utility of ST2 measurement for evaluation of dyspneic patients was assessed.

The subjects used in this Example took part in the ProBNP Investigation of Dyspnea in the Emergency Department (PRIDE) Study, a prospective, blinded study of 599 dyspneic subjects presenting to the ED of the Massachusetts General Hospital, and was performed for the purpose of validation of the diagnostic and prognostic use of NT-proBNP testing. The results of the PRIDE study were recently reported (Januzzi et al., Am. J. Cardiol. 95(8):948-54 (2005)).

The gold standard for the diagnosis of acute HF was based on the impression of reviewing physicians, blinded to NT-proBNP values, who had all available information from presentation through the 60-days of follow-up; for the few patients in whom a diagnosis was uncertain, the reviewers were instructed to utilize the guidelines as reported by the Framingham Heart Study (McKee et al., N. Engl. J. Med. 285(26):1441-6 (1971)).

As reported, 209 subjects (35%) in the PRIDE study were adjudicated to have dyspnea due to acute destabilized HF, of whom 17 had mild (Class II) symptoms by the New York Heart Association (NYHA) classification, 80 had moderate (Class III) symptoms, and 112 had severe (Class IV symptoms). Of those without acute HF, the most common diagnoses were exacerbation of obstructive airways disease (n=150; includes exacerbation of chronic obstructive pulmonary disease (n=120) and asthma (n=30) as well as acute pneumonia (n=64).

At the end of one year, the managing physician for each patient was contacted to ascertain the vital status of the patient. As reported, follow-up at one year was complete in 597 subjects overall (Januzzi et al., Arch Intern Med 2006; 166(3):315-20).

NT-proBNP was measured in the PRIDE study using a commercially available immunoassay (ELECSYS® ProBNP assay, Roche Diagnostics, Indianapolis, Ind.), using established methodology. In the PRIDE study, the assay had inter-run coefficients of variation of 0.9%. Blood collected at the time of presentation was later analyzed for concentrations of ST2, using an enzyme-linked immunosorbant assay (Medical & Biological Laboratories Co., Ltd.), as described in Example 1 herein. This assay utilizes monoclonal antibodies to human ST2 for both capture and detection, and had a relative percent difference of 17.5% in the present analysis. The plasma used for the present study had been previously subjected to a single freeze-thaw cycle.

Comparisons Between Groups

Comparisons of clinical characteristics between patients were performed utilizing chi-square tests for categorical data and the Wilcoxon rank-sum test for continuous data. Comparisons of ST2 concentrations between diagnostic, New York Heart Association (NYHA) symptom classes and outcome categories were performed using non-parametric testing.

Correlations

ST2 and NT-proBNP results were log-transformed to establish normal distribution. Correlations between these log-transformed variables were evaluated with the Spearman correlation coefficient. There was a modest correlation between concentrations of log-transformed ST2 and log-NT-proBNP in all subjects (r=0.58, p<0.001), those without acute HF (r=0.47, p<0.001) and those with acute HF (r=0.40, p<0.001).

Cut-Point Analyses

Patient characteristics as a function of an ST2 concentration of above or below 0.20 ng/ml are detailed in Table 3, which demonstrates the expected prevalence of factors consistent with a diagnosis of incident HF.

TABLE 3

Characteristics of Study Subjects as a Function of ST2 Concentrations

| Characteristic | ST2 ≥ 0.2 ng/ml (n = 320) | ST2 < 0.2 ng/ml (n = 279) | P value |
|---|---|---|---|
| Age (mean ± SD), years | 67.7 ± 15.0 | 56.5 ± 17.5 | <0.001 |
| Past medical history | | | |
| Prior cardiomyopathy | 13% | 7% | 0.02 |
| Prior congestive heart failure | 37% | 12% | <0.001 |
| Arrhythmia | 20% | 13% | 0.02 |
| Hypertension | 54% | 43% | 0.009 |
| Diabetes mellitus | 35% | 16% | <0.001 |
| Coronary artery disease | 33% | 22% | 0.005 |
| Myocardial infarction | 15% | 11% | NS |
| Obstructive airway disease | 15% | 8% | 0.005 |
| Symptoms/signs | | | |
| Paroxysmal nocturnal dyspnea | 16% | 8% | 0.002 |
| Orthopnea | 22% | 12% | 0.001 |
| Lower extremity edema | 26% | 7% | <0.001 |
| Chest pain | 35% | 52% | <0.001 |
| Dyspnea at rest | 50% | 24% | <0.001 |
| Medications at presentation | | | |
| Beta blocker | 44% | 32% | 0.002 |
| Loop diuretic | 41% | 17% | <0.001 |
| Digoxin | 13% | 8% | 0.04 |
| Angiotensin converting enzyme inhibitor | 25% | 16% | 0.009 |
| Physical examination | | | |
| Body-mass index (Kg/m$^2$, mean ± SD) | 28.0 ± 7.0 | 28.5 ± 6.5 | NS |
| Pulse, beats per minute (mean ± SD) | 91.7 ± 23.8 | 82.9 ± 20.6 | <0.001 |
| Jugular venous distension | 13% | 4% | <0.001 |

TABLE 3-continued

Characteristics of Study Subjects as a Function of ST2 Concentrations

| Characteristic | ST2 ≥ 0.2 ng/ml (n = 320) | ST2 < 0.2 ng/ml (n = 279) | P value |
|---|---|---|---|
| Murmur | 14% | 8% | 0.009 |
| Hepatojugular reflux | 3% | 0% | 0.002 |
| Lower extremity edema | 34% | 14% | <0.001 |
| Rales | 35% | 16% | <0.001 |
| Electrocardiographic findings | | | |
| Atrial fibrillation | 16% | 9% | 0.009 |
| Chest radiographic findings | | | |
| Interstitial edema | 25% | 8% | <0.001 |
| Pleural effusion | 28% | 5% | <0.001 |
| Cephalization of vessels | 2% | 0% | 0.04 |
| Laboratory findings | | | |
| Serum creatinine, mg/dl, mean ± SD | 1.2 ± 0.5 | 0.98 ± 0.3 | <0.001 |
| Creatinine clearance, ml/min/1.73 m$^2$, mean ± SD | 67.3 ± 32.0 | 85.2 ± 61.0 | <0.001 |
| Blood urea nitrogen, mg/dl, mean ± SD | 25.5 ± 17.0 | 17.2 ± 10.0 | <0.001 |
| Troponin T, ng/dl, mean ± SD | 0.063 ± 0.32 | 0.022 ± 0.16 | 0.04 |
| NT-proBNP, pg/ml, median (IQR) | 1800 (365-6745) | 97 (40-477) | <0.001 |

These results indicate that ST2 is not generally correlated with BMI, but is associated with a number of other indices including serum creatinine levels and clearance, prior congestive heart failure, and diabetes mellitus.

Example 3

Measurement of Soluble ST2 Concentrations for the Determination of Risk of Death in Patients with Acute Dyspnea Factors predictive of mortality within one year following presentation with dyspnea were evaluated in the population described in Example 2. Candidate ST2 diagnostic cut points were evaluated with the use of bootstrapping techniques using the STATA SWBOOT program; this was followed by multivariable logistic regression analyses. Each of the estimation procedures was coded in programming language then subjected to the STATA bootstrap prefix command for 10 bootstrap repeated random samples, followed by 100 replications for those variables selected in the initial analyses. The bootstrap sample size was 593 (the size of the entire data set). Factors entered into the analysis included elements from past and present medical history, symptoms and signs, medication use, as well as results of diagnostic studies including radiographic studies, electrocardiography, hematology, and blood chemistries. Measures of renal function included serum creatinine results as well as estimated glomerular filtration rate (Levey et al., Ann. Intern. Med. 130(6):461-70 (1999)). Following, candidate predictors of mortality (i.e., those with greater than 70 selections in bootstrap replications) were entered into multivariable logistic regression analyses, with acute HF as the dependent variable. For each logistic regression, results were entered in a single forward step with tail-probability to enter set at p=0.01 and to remove the effect from the regression at p=0.02, and goodness-of-fit was evaluated using the Hosmer-Lemeshow test.

In mortality analyses including NT-proBNP, this variable was modeled dichotomously, with a threshold value of 986 pg/ml for predicting death within one year, as identified previously (Januzzi et al., 2006, supra). After the SWBOOT run, the resulting validated candidate independent variables were entered stepwise into a Cox Proportional Hazards model; the proportions for this model were checked and were found to be appropriate. Hazard ratios (HR) with 95% CI (confidence interval) were generated for each independent predictor of death by one year.

Kaplan-Meier survival curves were constructed to compare mortality rates within one year in groups divided as a function of ST2 concentrations (as well as diagnosis), using the log-rank test to compare the significance of the rates of mortality.

For all statistical analyses, either SPSS (Chicago, Ill., USA) or STATA (College Station, Tex.) software was used; all p values are two-sided, with composite results<0.05 considered significant.

Within one year, 93 subjects (15.7%) had died. The median concentrations of ST2 were significantly higher among decedents (1.03 ng/ml, IQR (interquartile range) =0.38-2.43) than survivors (0.18 ng/ml, IQR=0.08-0.51; p<0.001). This pattern of higher ST2 concentrations in decedents remained when subjects were considered as a function of the absence of acute HF (1.14 vs 0.13 ng/ml; p<0.001), as well as in those with acute HF (0.90 vs 0.45 ng/ml; p<0.001).

Receiver operating characteristic (ROC) curve analysis using Analyse-It software (Analyse-It, Ltd, Leeds, UK) was performed for ST2, using the gold standard diagnosis of HF or survival within one year as the reference standard, and area under the curve (AUC) was estimated; following, potential cut points for both diagnosis and prognosis were identified, and their sensitivity, specificity, as well as positive and negative predictive values (PPV, NPV) were estimated. To further evaluate the utility of optimal ROC-optimal cut-points, patients were also divided into deciles based on their ST2 concentrations, and evaluated for ST2 threshold effects on the frequency of mortality.

Figure 2:
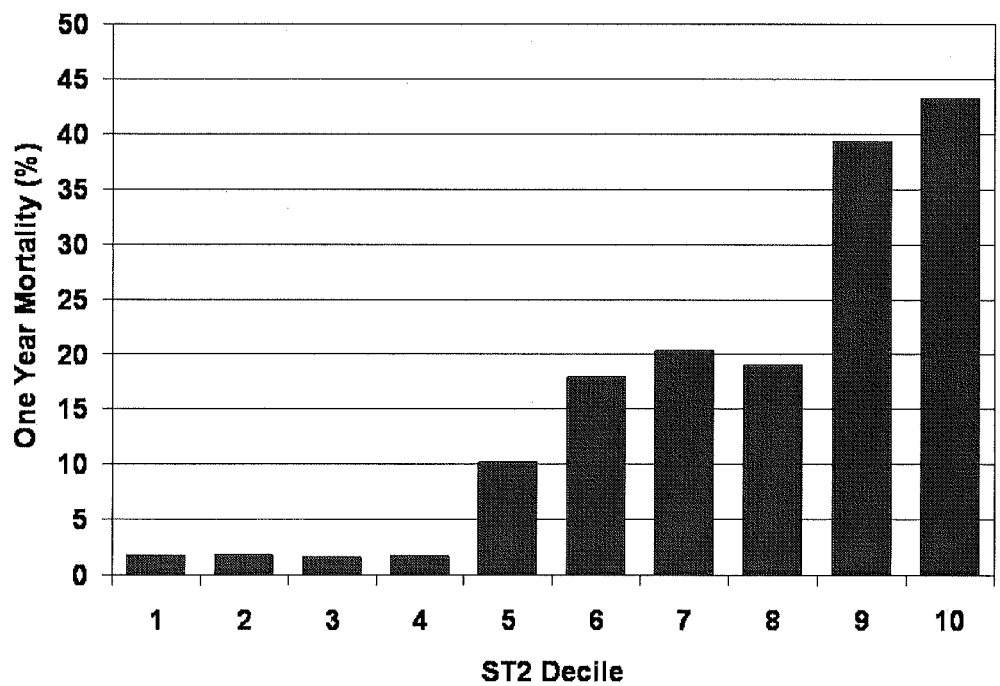
FIG. 2 is a bar graph illustrating the crude rates of death across deciles of ST2 in the ProBNP Investigation of Dyspnea in the Emergency Department (PRIDE) study cohort. A clear threshold effect is noted at decile 5, corresponding to an ST2 concentration of 0.23 ng/ml for the particular assay.

ROC analyses demonstrated an AUC of 0.80 (95% CI=0.75-0.84, p<0.001) for ST2 and one year mortality (FIG. 1); the optimal cut point as identified by ROC was 0.29 ng/ml, which was 87% sensitive (95% CI=79-93%), 63% specific (95% CI=58-67%), and had a PPV of 30% and NPV of 96%. In decile analyses, a threshold effect for mortality was noted at the ST2 median of 0.20 ng/ml (FIG. 2). A graded relationship between ST2 concentrations and the likelihood for death was also found, such that those subjects below the median concentration of ST2 (n=236) enjoyed the lowest rates of death (2%) compared to those in the highest two deciles (n=117) who demonstrated a 42% rate of death within one year, a HR of 43.0 (95% CI=15.0-123.0, p<0.001).

In a final bootstrap model for prediction of death within one year (Table 4), an ST2 concentration≥0.20 ng/ml was selected in 96 of 100 replications and represented the strongest predictor of death within one year in breathless patients (HR=5.6, 95% CI=2.2-14.2; p<0.001). Notably, even with the inclusion of NT-proBNP into the models, an ST2≥0.20 ng/ml remained the most selected variable in bootstrap replications (86 of 100 selections), and remained the strongest predictor of death within one year (HR=4.6, 95% CI=1.8-11.8; p=0.002).

TABLE 4

Identification of Independent Predictors of Death Within One Year in Dyspneic Subjects

| Variable | Bootstrap Analysis Number selected out of 100 replications | Multivariable analysis Hazard ratio | Multivariable analysis 95% confidence intervals | Multivariable analysis P value |
|---|---|---|---|---|
| Without NT-proBNP in the model | | | | |
| Log-transformed ST2 | 99 | 2.7 | 1.6-4.4 | <0.001 |
| ST2 ≥ 0.20 ng/ml | 96 | 5.6 | 2.2-14.2 | <0.001 |
| Hemoglobin | 73 | 0.91 | 0.85-0.98 | 0.008 |
| Pleural effusion on chest X-ray | 95 | 1.8 | 1.2-2.8 | 0.005 |
| With NT-proBNP in the model | | | | |
| ST2 ≥ 0.20 ng/ml | 86 | 4.6 | 1.8-11.8 | 0.002 |
| NT-proBNP ≥ 986 pg/ml | 85 | 2.3 | 1.3-4.0 | 0.002 |
| Cough | 80 | 0.60 | 0.39-0.95 | 0.03 |
| Pleural effusion on chest X-ray | 80 | 1.6 | 1.0-2.4 | 0.05 |
| Log-transformed ST2 | 77 | 2.6 | 1.6-4.4 | <0.001 |

The results of Table 4 are based on 100 bootstrap replications, followed by multivariable Cox Proportional Hazards analysis are shown in the absence and presence of NT-proBNP results in the model. Only those variables selected >70 of 100 times in bootstrap replications are shown.

Figure 3A:
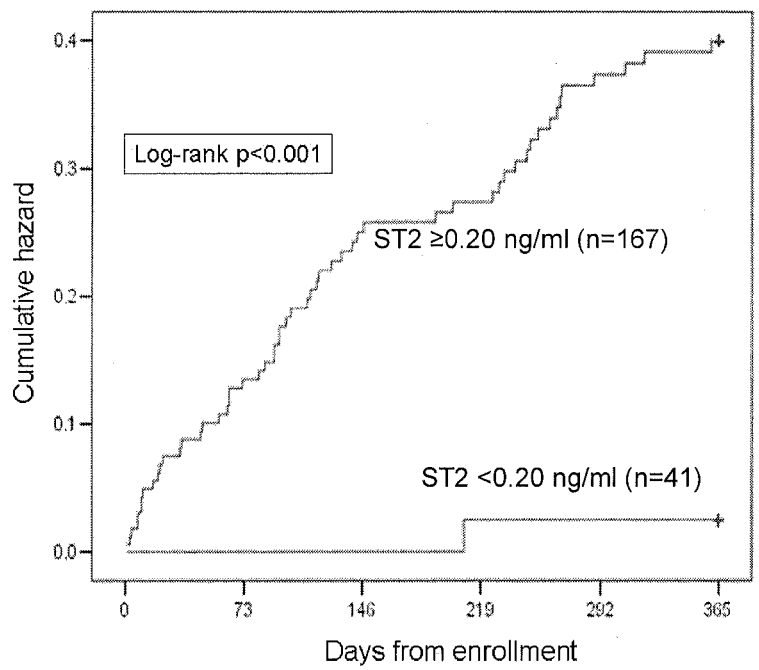
FIGS. 3A and 3B are a pair of Kaplan-Meier hazard curves depicting the rates of death from presentation to one year of follow up in patients with dyspnea, stratified as a function of ST2 concentrations. Among dyspneic patients with ST2 concentrations of ≥0.20 ng/ml, a high rate of mortality was noted within days of presentation, and extending to a full year from presentation. The rates of death were similar among those with (3A) and without (3B) acute heart failure (all Log-rank p values<0.001).
Figure 3B:
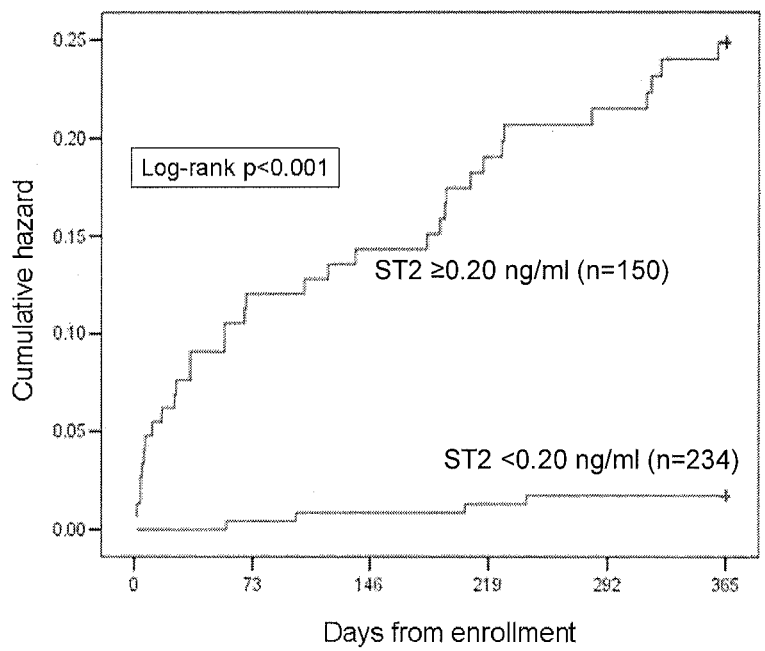

Kaplan-Meier hazard curves demonstrate that among subjects with ST2 concentrations≥0.20 ng/ml, rates of death rose rapidly from enrollment, and continued to rise within one year (FIG. 3A; Log rank p value<0.001). Similar relationships between ST2 values≥0.20 ng/ml in those without and with the diagnosis of acute HF at presentation (FIG. 3B; Log-rank p value for both <0.001).

Therefore, ST2 levels are an excellent predictor of mortality.

Example 4

Measurement of Soluble ST2 and NT-proBNP Concentrations for the Determination of Risk of Death in Patients with Acute Dyspnea As ST2 and NT-proBNP were both independent predictors of death within one year, crude rates of death in subjects as a function of ST2 and NT-proBNP concentrations were examined using the methods described above. The percentage of subjects who died in each category are shown in Table 5.

TABLE 5

Mortality Rates as a Function of NT-proBNP and ST2 Concentrations in the PRIDE Study

| | ST2 < 0.20 ng/ml | ST2 ≥ 0.20 ng/ml |
|---|---|---|
| NT-proBNP < 986 pg/ml | 1.7% | 13.1% |
| NT-proBNP ≥ 986 pg/ml | 4.5% | 37.0% |

Figure 4:
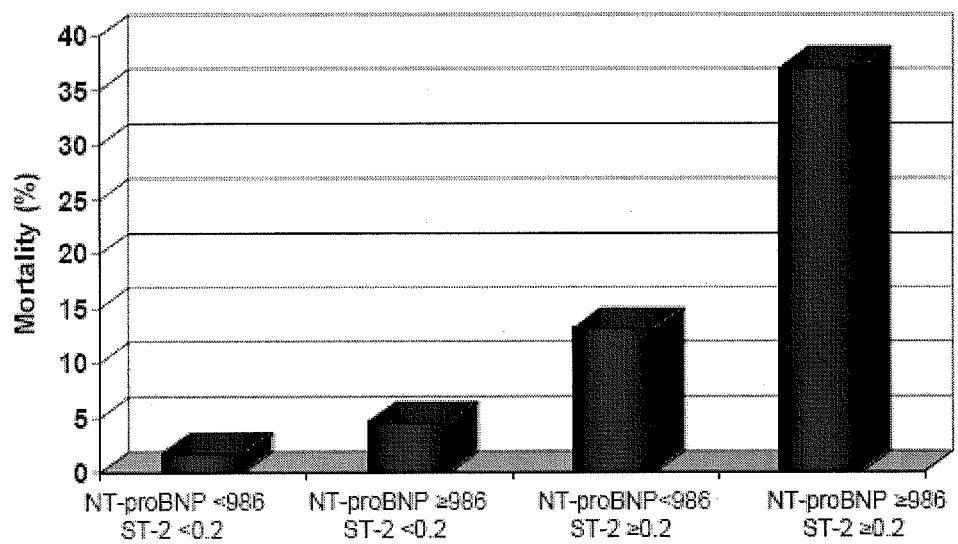
FIG. 4 is a bar graph illustrating mortality rates as a function of marker concentrations for NT-proBNP and ST-2.

The majority of mortality among subjects in the PRIDE study occurred in those with elevated levels of ST2 (equal to or above 0.20 ng/ml) and NT-proBNP (equal to or above 986 pg/ml) (Table 5 and FIG. 4).

Thus, the combination of NT-proBNP and ST2 levels is useful in predicting risk of mortality.

Example 5

Elevated ST2 Concentrations in Patients in the Absence of MI

ST2 concentrations were determined as described in Example 1, above, in a population of 350 patients who presented to the ED with chest pain. Serum samples were obtained and ST2 measurements made at baseline, and 90 and 180 minutes later for most patients. Also, for most patients, the baseline sample was collected within 2 hours of onset of symptoms.

17 patients had final diagnosis of MI, and 5 of these had ST2≥0.23 (0.25-0.65). Two of these patients were troponin negative. 11 patients had very high ST2 levels (0.97-9.22), but none of these patients had confirmed final diagnosis of MI, though all had severe diseases, including COPD, lymphoma, sepsis, alcohol abuse, and pulmonary embolism. The diagnoses for these 11 patients are shown in Table 6; ST2 1 is the baseline level, ST2 2 is 90 minutes later, and ST2 3 is at 180 minutes.

TABLE 6

Non-MI Patients with High ST2 Levels

| Patient | ST2 1 (ng/ml) | ST2 2 (ng/ml) | ST2 3 (ng/ml) | Final Diagnosis |
|---|---|---|---|---|
| 811 | 1.43 | 1.62 | 1.63 | COPD with heart failure following coronary artery bypass graft surgery and pulmonary hypertension |
| 847 | 2.37 | 4.44 | 3.53 | Pulmonary embolism |
| 873 | 2.36 | 2.42 | 2.74 | RAD |
| 898 | 1.32 | 1.24 | 1.66 | History of heart failure following coronary artery bypass surgery |
| 920 | 6.03 | 9.22 | | Bacteremia sepsis |
| 928 | 3.80 | 4.69 | 3.99 | Hypertension and alcohol abuse |
| 952 | 6.76 | | | Alcohol abuse, gastritis and pulmonary hypertension |
| 953 | 3.77 | | | History of heart failure following coronary artery bypass surgery |
| 1055 | 1.42 | 1.28 | 1.13 | URI |
| 1213 | 0.97 | 1.19 | 1.07 | Pulmonary embolism and pericarditis |
| 1245 | 4.11 | 6.46 | | Lymphoma and hypertension |
| 1280 | 1.30 | 1.33 | | COPD |

These results demonstrate that elevated ST2 is associated with severe disease, regardless of the underlying pathology.

Example 6

Serial Analysis of ST2 Concentrations in Patients Hospitalized with Acute Decompensated Heart Failure (ADHF)

ST2 concentrations were determined as described in Example 1, above, as were BUN, NT-Pro-BNP, and BNP, in a population of 150 subjects who were diagnosed with and admitted for acute decompensated heart failure (ADHF) to the San Diego Veterans' Administration Hospital. Some patients had a new diagnosis of ADHF and other patients had an acute exacerbation of existing heart failure. Samples were taken on successive days in a number of patients, though not every patient gave a sample every day. Length of stay (LOS) in the hospital for these patients ranged from 1 to 24 days with an average of 5 days. Table 7 shows the characteristics of the population; as expected, given that the population was drawn from the San Diego Veteran's Hospital, the population was overwhelmingly male and Caucasian.

TABLE 7

Frequency of Patient Characteristics

|  | Frequency | Percent |
|---|---|---|
| Gender |  |  |
| Male | 148 | 98.7 |
| Female | 2 | 1.3 |
| Total | 150 | 100 |
| Ethnicity |  |  |
| White | 115 | 76.6 |
| Black | 22 | 14.7 |
| Hispanic | 9 | 6 |
| Asian | 3 | 2 |
| other | 1 | 0.7 |
| Total | 150 | 100 |
| Diagnosis |  |  |
| CHF new | 14 | 9.3 |
| CHF worse | 110 | 73.3 |
| Other | 26 | 17.3 |
| NYHA* |  |  |
| Class II | 9 | 6 |
| Class III | 75 | 50 |
| Class IV | 66 | 44 |
| Etiology |  |  |
| Unknown | 61 | 40.7 |
| Ischemic | 43 | 28.7 |
| Hypertensive | 23 | 15.3 |
| Other | 9 | 6.1 |
| Alcohol | 5 | 3.3 |
| Idiopathic | 3 | 2 |
| Valve | 1 | 0.7 |
| Drug | 1 | 0.7 |

*NYHA = New York Heart Association Stages of Heart Failure: Class I: No limitation of physical activity. Ordinary physical activity does not cause undue fatigue, palpitation, or dyspnea (shortness of breath). Class II: Slight limitation of physical activity. Comfortable at rest, but ordinary physical activity results in fatigue, palpitation, or dyspnea. Class III: Marked limitation of physical activity. Comfortable at rest, but less than ordinary activity causes fatigue, palpitation, or dyspnea. Class IV: Unable to carry out any physical activity without discomfort. Symptoms of cardiac insufficiency at rest. If any physical activity is undertaken, discomfort is increased.

The population of patients was followed for at least 90 days, and adverse events were tabulated. A summary of events is shown in Table 8.

TABLE 8

Summary of Events

|  | Frequency | Percent |
|---|---|---|
| In hospital mortality | 8 | 5.3 |
| 30 day readmission | 13 | 8.7 |
| 30 day mortality CHF | 10 | 6.7 |
| 30 day mortality other | 7 | 4.7 |
| 90 day readmission | 26 | 17.3 |
| 90 day mortality CHF | 26 | 17.3 |
| 90 day mortality other | 9 | 6.0 |

*90 day outcome frequency is cumulative of all events that occurred at earlier time points.

Receiver operating characteristics and area under the curve (AUC) were determined as described herein for the correlation of levels of BNP, NT-ProBNP, and ST2 at admission and at discharge with the adverse events listed in Table 8. The results are shown in Table 9. AUC for ST2 change from first to last=0.820.

TABLE 9

ROC SUMMARY (AUC)

|  | In Hospital mortality | 30 day event | 30 day mortality | 90 day event | 90 day mortality |
|---|---|---|---|---|---|
| BNP Admit | 0.735 | 0.536 | 0.630 | 0.569 | 0.653 |
| BNP Discharge | NA | 0.545 | 0.648 | 0.575 | 0.692 |
| NT-proBNP Admit | 0.790 | 0.638 | 0.785 | 0.624 | 0.763 |
| NT-proBNP Discharge | NA | 0.637 | 0.831 | 0.631 | 0.815 |
| ST2 admit | 0.638 | 0.549 | 0.574 | 0.558 | 0.603 |
| ST2 Discharge | 0.752 | 0.642 | 0.760 | 0.657 | 0.772 |
| Change in ST2 | NA | 0.573 | 0.793 | 0.604 | 0.809 |

In this small and extremely homogeneous population, the biomarkers that most accurately predicted the reported events included change in ST2 for 30 and 90 day mortality, and NT-proBNP levels at discharge for both 30 and 90-day mortality. As expected, the homogeneity of this cohort resulted in the AUC using the admission measurement for each biomarker being lower than what was observed in the PRIDE cohort (described in examples 2-3). The high number of patients without diagnosed heart failure reported in the PRIDE cohort resulted in a high discriminatory power of ST2 at the admission measurement. In this specialized cohort, where every patient already had a diagnosis of heart failure, the ST2 level at admission is expected to be somewhat elevated; consequently, the predictive power for subsequent events is somewhat diminished as compared to a heterogenous cohort that is more representative of the general population.

A univariate model of predictors of 90 day mortality was analyzed including the same markers, as well as BUN and creatinine clearance, which are markers of renal function. The results are shown in Table 10.

TABLE 10

Univariate Predictors of 90-day Mortality

| Predictor | Odds Ratio | P-Value |
|---|---|---|
| Change in ST 2: ≥−0.02 vs. <−0.02 | 11.55 | 0.002 |
| Admission ST 2: ≥0.2 vs. <0.2 | 1.14 | 0.83 |
| Discharge ST 2: ≥0.2 vs. <0.2 | 7.00 | 0.003 |
| Admission BNP: ≥400 vs. <400 | 1.91 | 0.35 |
| Discharge BNP: ≥400 vs. <400 | 2.59 | 0.14 |
| Admission NT-ProBNP: ≥5000 vs. <5000 | 3.96 | 0.09 |
| Discharge NT-ProBNP: ≥5000 vs. <5000 | 6.72 | 0.007 |
| Admission BUN continuous | 1.033 | 0.002 |
| Admission creatinine continuous | 1.50 | 0.07 |

In this analysis, for the dichotomous variables (all but BUN and creatinine) the odds ratio represents the increased odds of death within 90 days for a positive test vs. a negative test. For the continuous variables (BUN and creatinine) the odds ratio represents the increased odds of death within 90 days for each 1 mg/dL increase. As shown in Table 10, change in ST2 provided the best indication of 90 day mortality, with an OR of 11.55 (p=0.002).

A multivariate model was also constructed that included BNP, NT-ProBNP, BUN and creatinine clearance levels with change in ST2. The results are shown in Table 11.

TABLE 11

Predictors of 90-day Mortality With Change in ST2

| Additional Predictor in Model | Change in ST 2 Odds Ratio | P-Value | Additional Predictor Odds Ratio | P-Value | Model $R^2$ |
|---|---|---|---|---|---|
| Admission BNP | 12.18 | 0.002 | 2.04 | 0.34 | 0.246 |
| Discharge BNP | 13.98 | 0.001 | 3.56 | 0.07 | 0.285 |
| Admission NT-ProBNP | 14.49 | 0.001 | 5.48 | 0.044 | 0.312 |
| Discharge NT-ProBNP | 10.04 | 0.005 | 5.49 | 0.021 | 0.325 |
| Admission BUN | 7.87 | 0.014 | 1.023 | 0.034 | 0.300 |
| Admission creatinine | 10.08 | 0.005 | 1.260 | 0.30 | 0.241 |

When only change in ST2 (the difference between the ST2 levels) was considered, the $R^2$ for the model was 0.223. As can be seen in Table 11, in each case change in ST2 was the stronger predictor due to its having the smaller p-value. Moreover, only admission NT-ProBNP, discharge NT-ProBNP, and admission BUN provided additional prediction beyond change in ST2 that achieved a statistical significance (p<0.05) (see bold $R^2$ values), while discharge BNP achieved marginal statistical significance (p=0.07).

Figure 5:
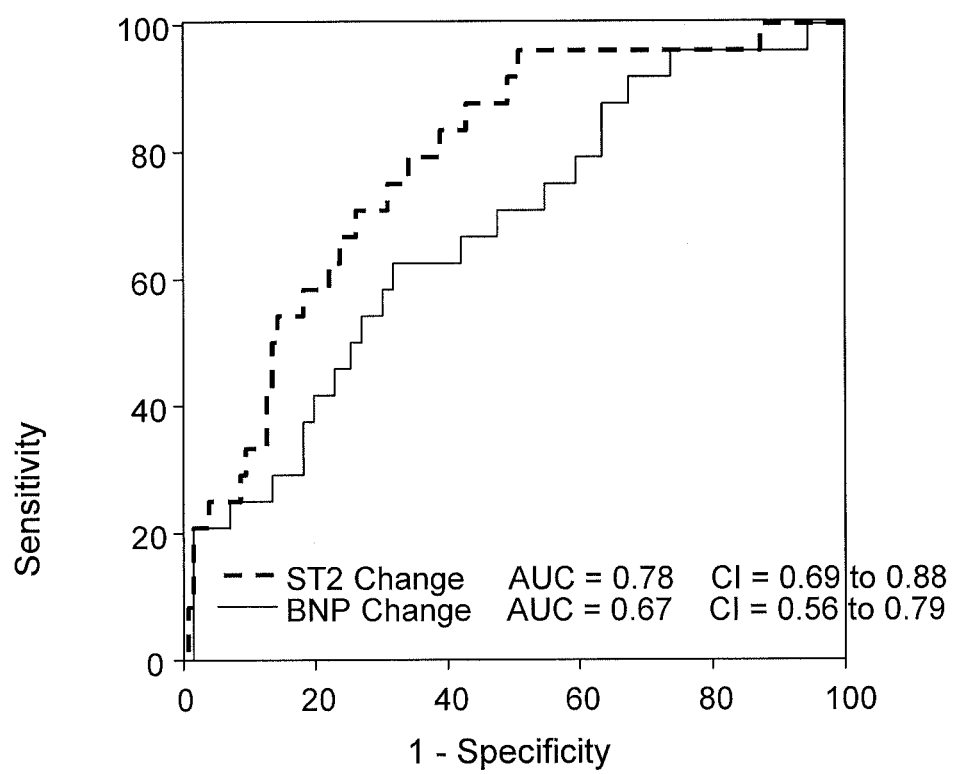
FIG. 5 is receiver operating curve (ROC) of specificity versus sensitivity, for change in ST2 (light grey line) and change in BNP (dark line).

Next, the ROC was compared for change in BNP and change in ST2. As shown in FIG. 5, the AUC for change in BNP during hospitalization was 0.67, while the AUC for change in ST2 was 0.78, significantly higher, indicating that change in ST2 is a much more accurate predictor of 90-day mortality than BNP.

Figure 6:
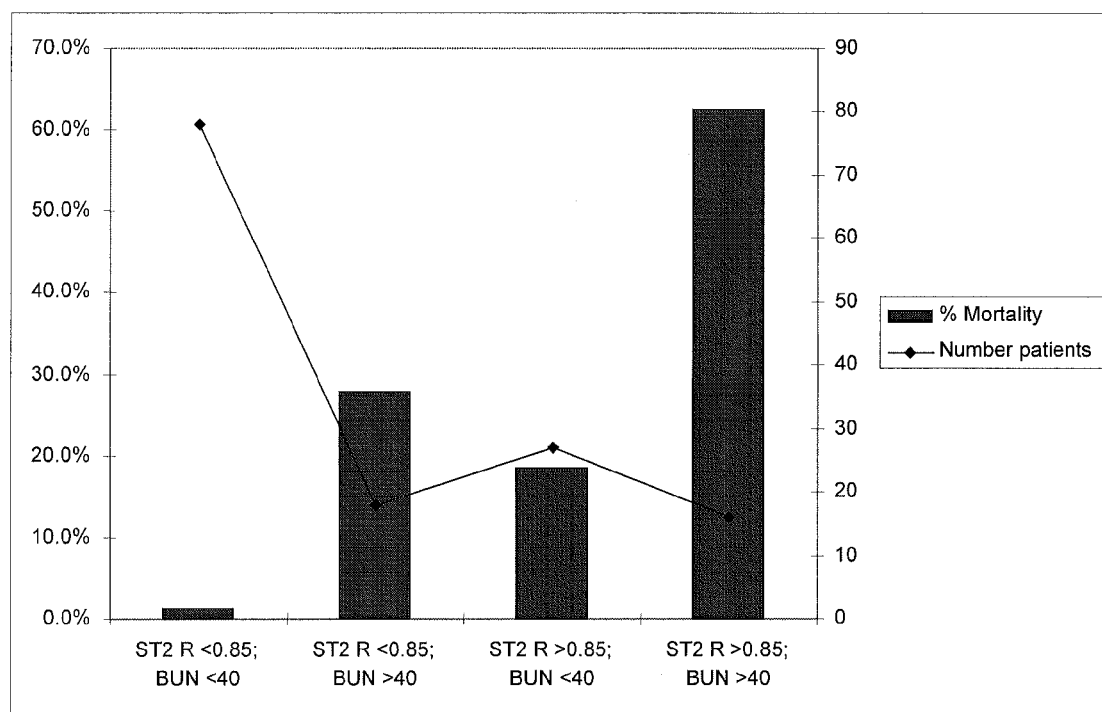
FIG. 6 is a combination bar and line graph. The bars illustrate the percent mortality in populations with the indicated levels of BUN and ST2 ratios. The line indicates the number of patients that are in each category.

The change in ST2 was analyzed in conjunction with BUN levels to determine whether the two markers, when used together provided additional predictive information. The results, shown in FIG. 6, demonstrate that BUN levels and changes in ST2 levels can be used to categorize patients by risk: patients with low levels of BUN (less than 40 mg/dL) and levels of ST2 that decreased by 15% or more had the lowest risk levels; patients with higher BUN and levels of ST2 that decreased by less than 15% (or increased or held steady) had the highest risk levels, while subjects with either high BUN and ST2 decreased by at least 15%, or low BUN and ST2 decreased by 15% or more, had a medium level of risk (which was still much increased over that of the lowest risk category, see FIG. 6).

Changes in ST2 levels over time were evaluated on a lapsed-time basis to determine an optimal length of time between first and second ST2 measurements. The results, shown in Tables 11A and 11B, indicate that a lapsed time of at least two days and within four days between the first and second measurement of ST2 provides the best information regarding likelihood of death within 90 days.

TABLE 11A

Summary of ST2 Values over Time

| | N | average | median |
|---|---|---|---|
| 1 day | 130 | 0.97 | 0.78 |
| 2 days | 99 | 1.00 | 0.60 |
| 3 days | 66 | 1.42 | 0.42 |
| 4 days | 44 | 1.87 | 0.57 |
| 5 days | 34 | 1.86 | 0.74 |

TABLE 11B

Correlation of ST2 Values with Mortality within 90 Days

| | N > 0.85 | # dead | % death | N < 0.85 | # dead | % death |
|---|---|---|---|---|---|---|
| 1 day | 54 | 7 | 13% | 76 | 7 | 9% |
| 2 days | 27 | 7 | 26% | 72 | 4 | 6% |
| 3 days | 19 | 4 | 21% | 47 | 2 | 4% |
| 4 days | 18 | 6 | 33% | 26 | 1 | 4% |
| 5 days | 14 | 6 | 43% | 20 | 1 | 5% |

In Table 11B, "N>0.85" indicates the number of people who had a reduction of less than 15% in ST2 over the time period indicated (so that the second level is 85% or more of the first level). After at least two days, the percentage of people with a ratio of 0.85 or higher who died was over 20% while the percentage of patients who died with a ratio below 0.85 initially decreased and remained low.

Figure 7A:
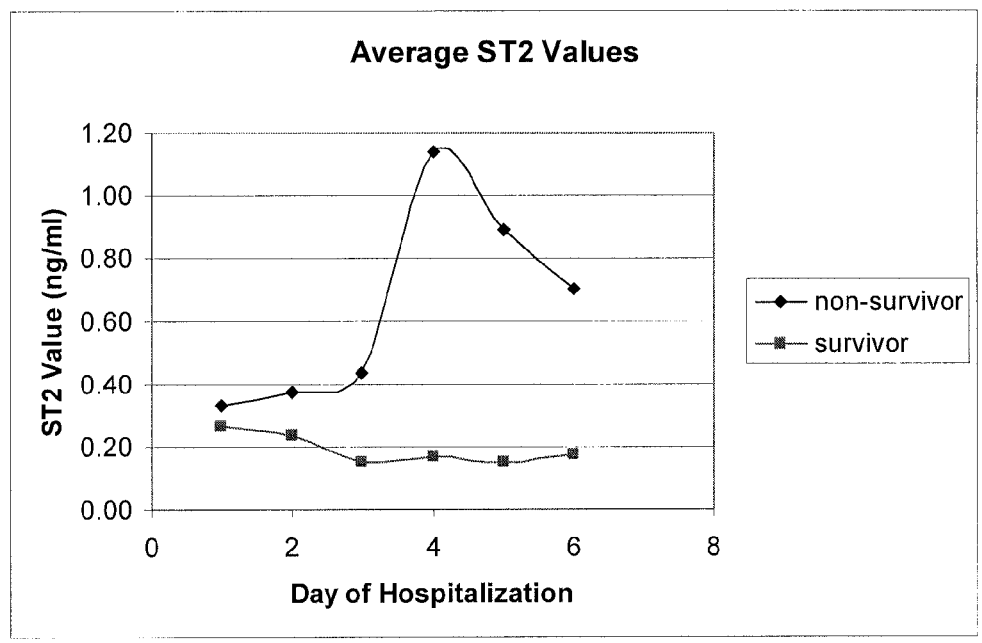
FIG. 7A is a line graph of average ST2 values for survivors (light grey squares) and non-survivors (dark diamonds) on each day of hospitalization.
Figure 7B:
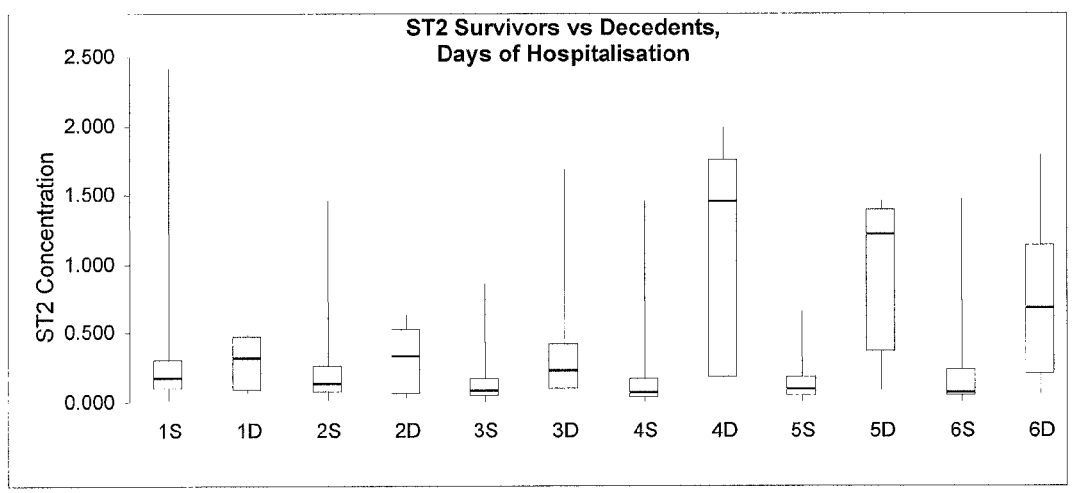
FIGS. 7B-7D are whisker box plots bracketing the 25th and 75th percentiles of ST2 levels (7B), BNP concentration (7C), and NT-proBNP (7D), plotted against time (over 6 days of hospitalization); S=survivors, D=decedents.
Figure 7C:
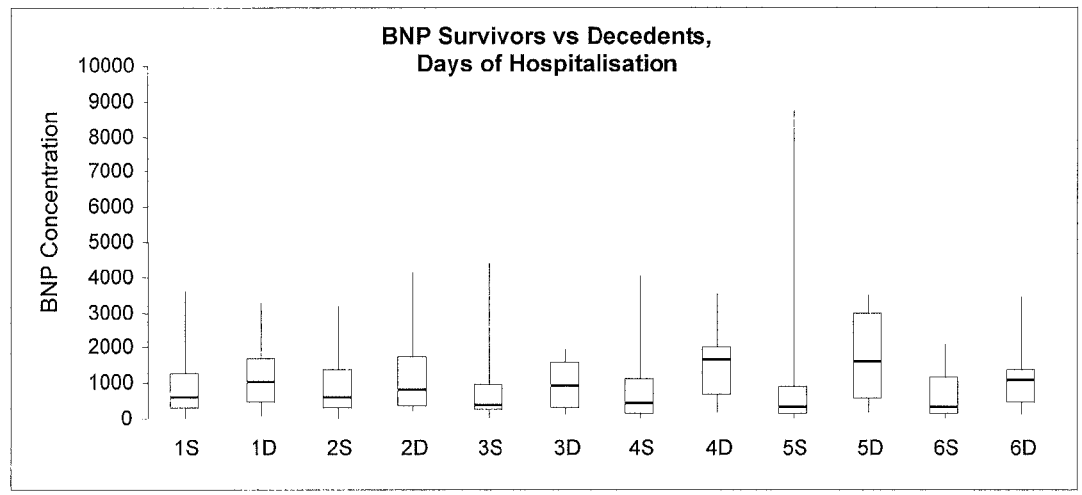
Figure 7D:
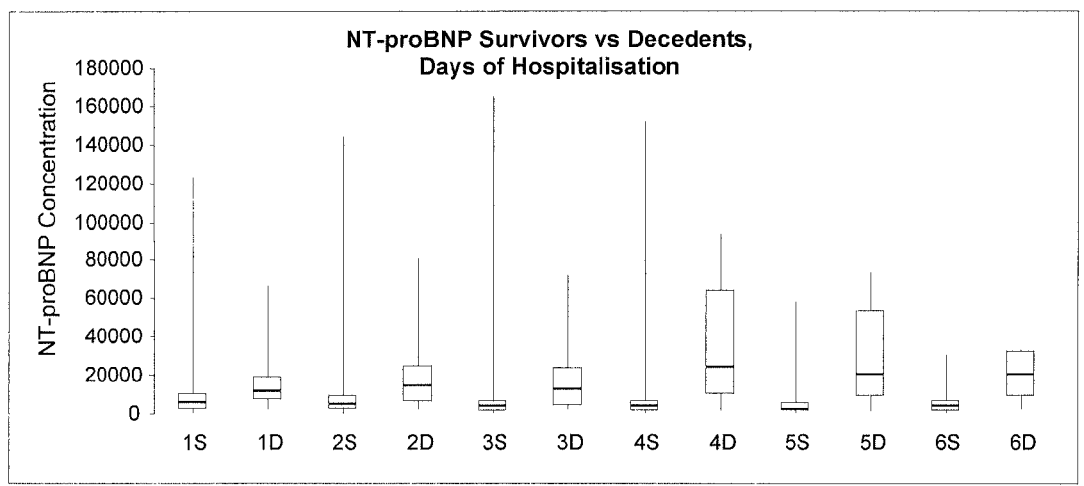

When average ST2 values over time were tracked in this population, a clear increase in correlation of risk of mortality within 90 days was seen at three to four days after the initial measurement was made, as shown in Table 12A and FIGS. 7A and 7B. FIG. 7B, a whisker box plot bracketing the $25^{th}$ and $75^{th}$ percentiles, illustrates that distinction between survivors and decedents is clearly resolved with the ST2 value. The ST2 results contrast with results generated by comparing either BNP or NT-proBNP over these same days of treatment. Although the mean values for each of these markers is distinct between survivors and decedents the groups are not statistically distinct from each other, as shown in FIGS. 7C and 7D. Unlike ST2 the survivor and decedent groups for BNP and NT-proBNP overlap significantly between the $25^{th}$ and $75^{th}$ percentiles. In this analysis ST2 is a more accurate marker than BNP or NT-proBNP alone for predicting mortality as a function of change over time during hospitalization.

Figure 8:
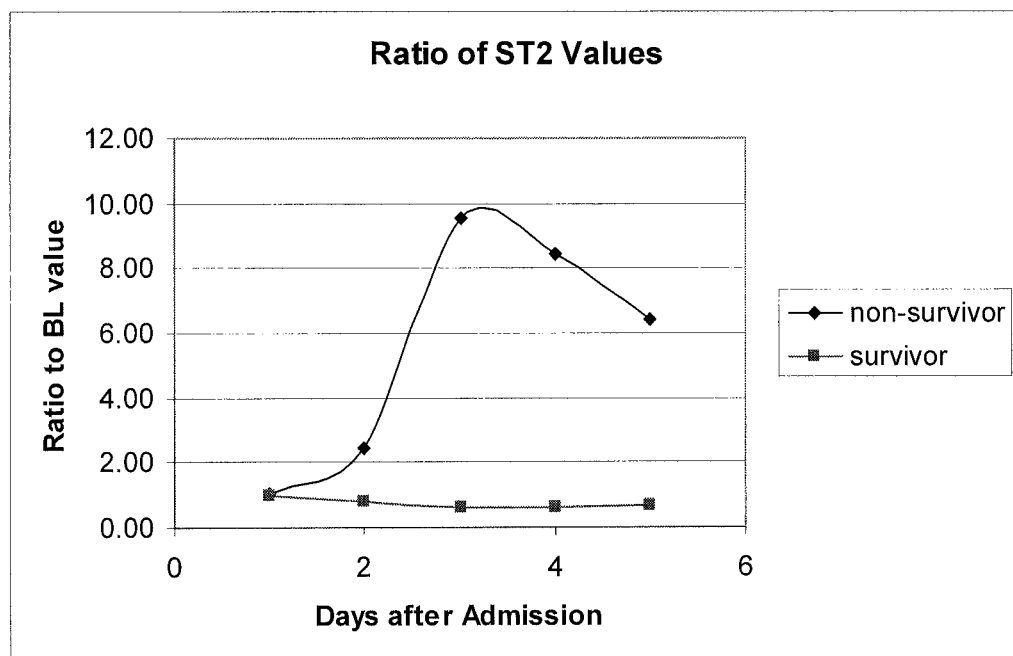
FIG. 8 is a line graph of ratios of ST2 values for survivors (light grey squares) and non-survivors (dark diamonds) as compared to baseline (around admission) on each day of hospitalization.

When average ratios of ST2 were calculated, again, a significant difference was seen; the results are shown in Table 12B and FIG. 8.

TABLE 12A

Average ST2 Values Over Time

| | Average ST2 value | | | | | |
|---|---|---|---|---|---|---|
| | ST2-1 | ST2-2 | ST2-3 | ST2-4 | ST2-5 | ST2-6 |
| non-survivor | 0.33 | 0.38 | 0.44 | 1.14 | 0.89 | 0.71 |
| survivor | 0.27 | 0.24 | 0.15 | 0.17 | 0.15 | 0.17 |

TABLE 12B

Change in ST2 Over Time

| | Average Ratio of ST2 | | | | |
|---|---|---|---|---|---|
| | 1 day | 2 days | 3 days | 4 days | 5 days |
| non-survivor | 1.04 | 2.44 | 9.57 | 8.43 | 6.46 |
| survivor | 0.96 | 0.82 | 0.60 | 0.63 | 0.67 |

It is also possible to use the ratio of ST2 along with the ratio of NT-proBNP in a 2×2 matrix analysis to further refine the risk stratification of these patients, as shown in Table 12C.

TABLE 12C

Change in ST2 and Change in NT-proBNP for Risk Stratification
NT-proBNP and ST2 ratios

|   | NT < 0.7, ST2 < 0.85 | NT < 0.7, ST2 > 0.85 | NT > 0.7, ST2 < 0.85 | NT > 0.7, ST2 > 0.85 |
|---|---|---|---|---|
| N | 45 | 7 | 34 | 28 |
| Mort | 0 | 2 | 3 | 6 |
| % Mort | 0.0% | 28.6% | 8.8% | 21.4% |

These results demonstrate that the change in ST2 over time is a powerful predictor of mortality, e.g., within 90 days, in both univariate or multivariate predictive analysis; change in ST2 was shown to be the strongest univariate predictor of patient outcome in this population, with optimal predictive value seen after 3 days of hospitalization. Combining change in ST2 data with a measure of renal function (e.g., BUN) provided additional predictive value, as did including an NT-proBNP measurement with change in ST2.

Example 7

ST2 Concentrations for Risk Stratification in Patients with Pulmonary Disease Of the 599 subjects in the PRIDE population (described in Examples 2 and 3), 209 had acute decompensated heart failure (ADHF). Of the remaining 390 subjects, 236 had "pulmonary disease"; of those with available data, 5 had uncomplicated bronchitis; 18 had pulmonary embolism (PE); 64 had pneumonia; and 149 had COPD/asthma. Of the 149 with COPD/asthma, 69 had asthma; 67 had emphysema; and 13 had chronic bronchitis.

To evaluate the usefulness of ST2 as a marker of risk in these patients, ST2 levels were assessed in each diagnostic category. Concentrations for each diagnostic category are shown in Table 13.

TABLE 13

ST2 Concentrations by Diagnosis

| Category | ST2 median | 25th-75th Percentile |
|---|---|---|
| Whole group | 0.23 | 0.09-0.69 |
| PE | 0.16 | 0.08-1.4 |
| Pneumonia | 0.69 | 0.14-2.29 |
| Bronchitis | 0.19 | 0.11-0.41 |
| Asthma/COPD | 0.20 | 0.08-0.54 |
| Asthma | 0.14 | 0.05-0.47 |
| Emphysema | 0.24 | 0.12-0.55 |
| Chronic bronchitis | 0.33 | 0.06-1.2 |

ST2 concentrations were evaluated using ROC analysis for death at one year, and concentrations in those dead and alive at one year were compared. Mortality rates as a function of ST2 concentrations to one year were analyzed. The results are shown in Table 14 and FIGS. 9-11.

TABLE 14

Mortality by Diagnosis

|   | PE | PNA | Acute bronchitis | Asthma/COPD |
|---|---|---|---|---|
| N | 18 | 64 | 5 | 149 |
| N survivors | 15 | 52 | 5 | 139 |
| ST2 survivors | 0.14 (0.07-0.36) | 0.53 (0.13-1.81) | See above | 0.17 (0.07-0.50) |
| ST2 decedents | 1.98 (1.2-3.83) | 1.17 (.4-3.17) | n/a | 0.31 (.2-1.1) |

Figure 9:
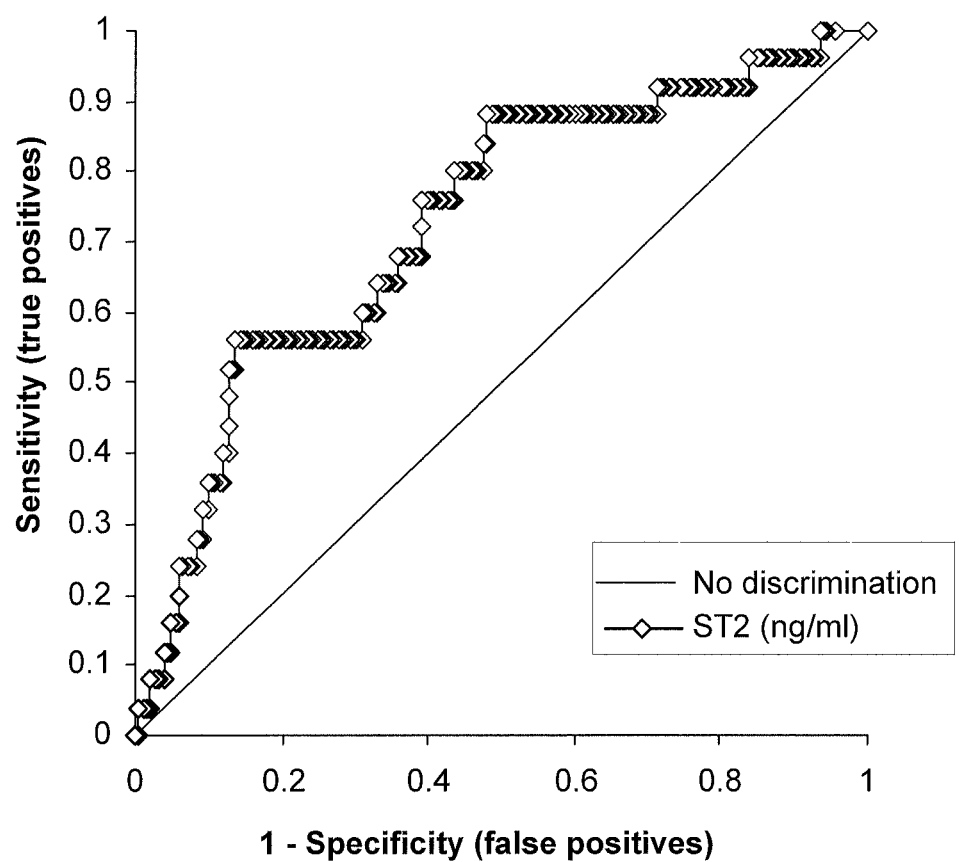
FIG. 9 is a ROC for ST2 ability to predict death by one year in PRIDE subjects with a pulmonary diagnosis. Area under ROC=0.73; 95% CI=0.62-0.83; P<0.0001; Optimal cut: 0.20 ng/ml; 88% sensitive, 52% specific; PPV=22%; NPV=96%.
Figure 10:
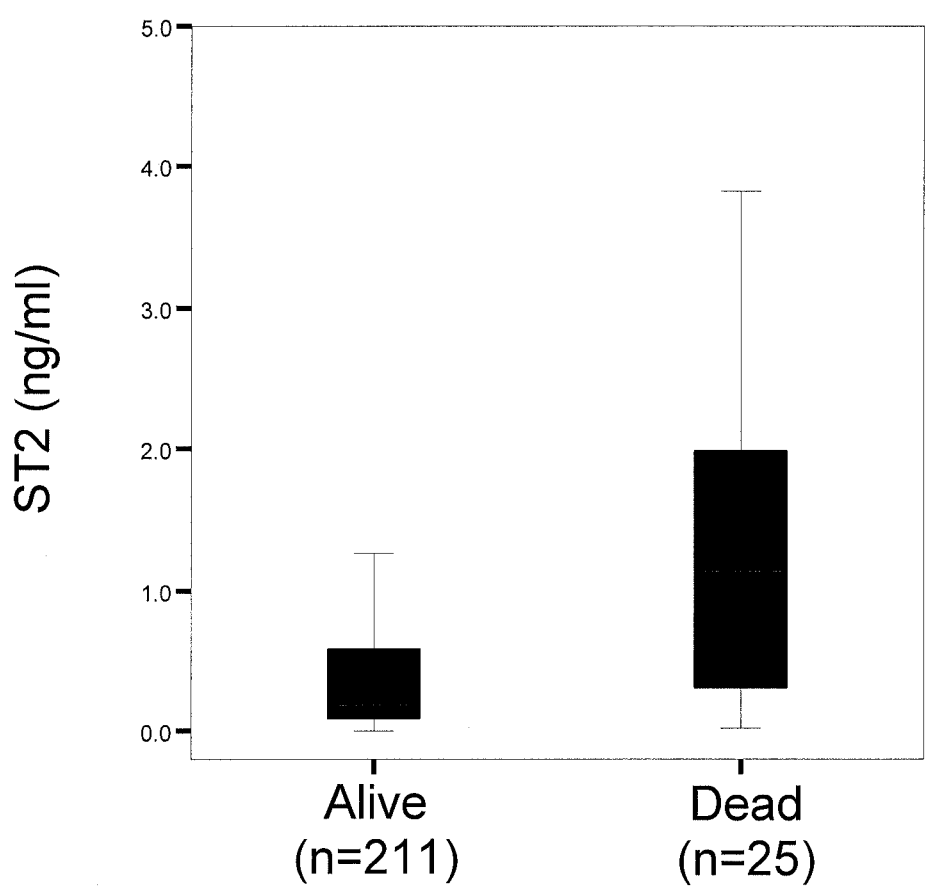
FIG. 10 is a box graph illustrating the correlation between ST2 concentrations and risk of death within one year in PRIDE subjects with a pulmonary diagnosis.
Figure 11:
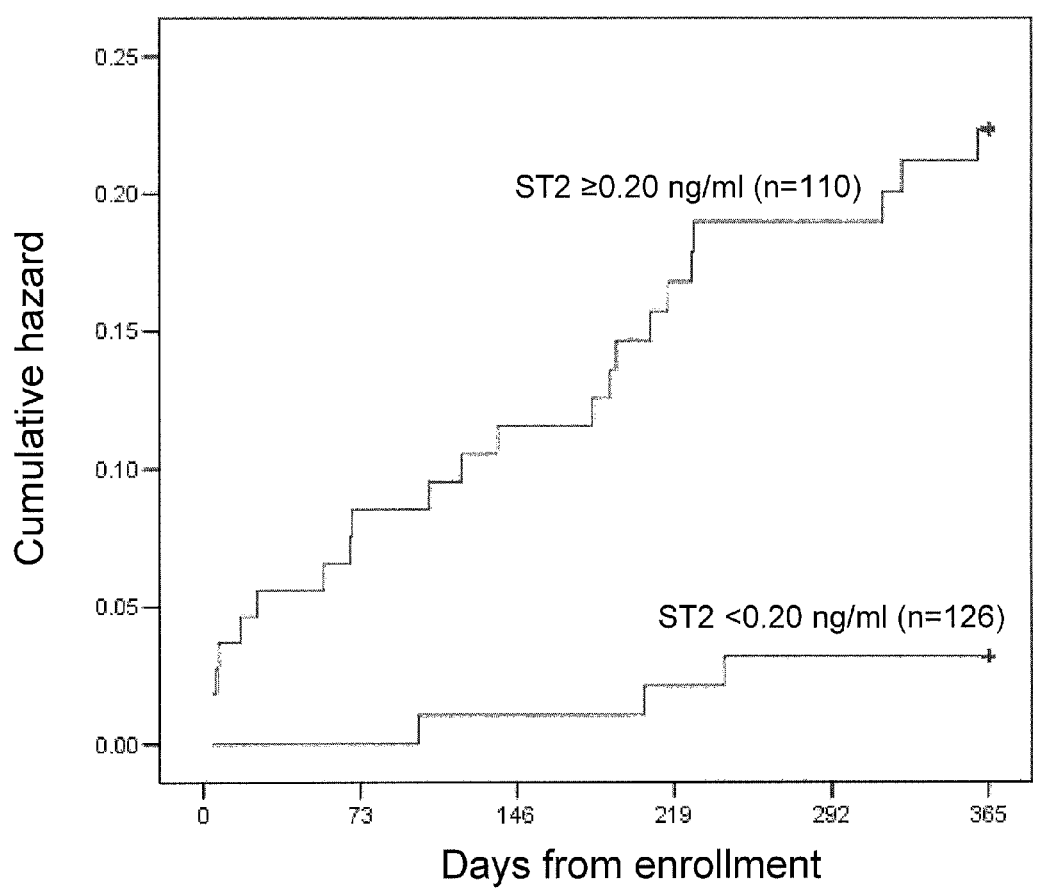
FIG. 11 is a line graph illustrating the mortality rate as a function of ST2 concentration in PRIDE subjects with a pulmonary diagnosis. P<0.001.

These results demonstrate that, as shown in FIG. 9, ST2 concentrations showed excellent specificity and sensitivity (Area under ROC=0.73; 95% CI=0.62-0.83; P<0.0001). The optimal cut point was 0.20 ng/ml, with 88% sensitivity and 52% specificity (PPV=22%; NPV=96%). FIG. 10 further illustrates this point. The median ST2 concentrations in subjects who were still alive at one year was 0.19 ng/ml (IQR 0.08-0.59, n=211); while median concentrations in subjects who had died within one year were 1.19 ng/ml (IQR 0.28-2.2, n=25). Finally, as shown in FIG. 11, mortality rate increased dramatically as a function of ST2 concentration, using a threshold of 0.2 ng/ml.

Multivariate Cox Proportional Hazards analyses were used to identify independent predictors of death at one year; the results are shown in table 15.

TABLE 15

Independent Predictors of Death in Pulmonary Disease

| Characteristic | Hazard ratio | 95% CI | P value |
|---|---|---|---|
| Age | 1.01 | 0.98-1.04 | 0.71 |
| Gender | 1.36 | 0.60-3.07 | 0.74 |
| ST2 ≥ 0.20 ng/ml | 6.14 | 1.80-21.0 | 0.004 |
| Pleural effusion on CXR | 2.99 | 1.30-6.83 | 0.009 |
| Emphysema | 0.29 | 0.13-0.65 | 0.003 |
| Spironolactone | 13.7 | 3.60-52.0 | <0.001 |

These data demonstrate that ST2 levels are an excellent predictor of death within one year, regardless of the underlying pathology, in subjects presenting with dyspnea.

Example 8

ST2 Concentrations are not Affected by Renal Insufficiency

The effect of renal impairment on ST2 concentrations was evaluated in a population of 135 patients with moderate to severe renal insufficiency. None of the patients were on dialysis, and none were previously diagnosed with CVD. All of the patients were evaluated using glomerular filtration rate (GFR in mls/min) as determined by the Modification of Diet in Renal Disease (MDRD) method as a measure of renal function. Echocardiography and coronary artery calcium (CAC) measurements were also performed on each subject to detect latent CVD. Multiple biomarkers were also evaluated.

The descriptive statistics for this cohort are shown in Table 16; the mean GFR and ST2 are illustrated graphically in FIGS. 12A-B.

TABLE 16

Glomerular Filtration Rate (GFR) and ST2 Levels

|  | GFR | ST2 levels (ng/ml) |
|---|---|---|
| Mean | 34.5 | 0.122 |
| Median | 34 | 0.107 |
| Std Error | 0.989 | 0.005 |
| Std Dev. | 11.4 | 0.059 |
| Coeff. Var. | 33.3 | 48.346 |
| Lower 95% CL | 32.5 | 0.112 |
| Upper 95% CL | 36.4 | 0.132 |
| 25th Percentile | 27 | 0.090 |
| 75th Percentile | 43 | 0.127 |
| Minimum | 9 | 0.068 |
| Maximum | 59 | 0.476 |
| Count | 135 | 135 |

In this cohort of patients with stable, chronic disease, only ten (8%) had ST2 levels above 0.2, the highest of which was 0.476 ng/ml. The distribution of ST2 values is shown in FIG. 13. This was as expected in this population of subjects with chronic, managed renal insufficiency; one would not expect to see very high ST2 levels.

Pearson Correlation analysis was performed in this population to determine whether there was a correlation between ST2 levels and GFR. The results are shown in Tables 17 and 18.

TABLE 17

Pearson Correlation Results - GFR and ST2

Descriptive Statistics

| Variable | Mean | Std Dev. | Std Err | N |
|---|---|---|---|---|
| GFR | 34.5 | 11.5 | 0.989 | 135 |
| ST2 (ng/mL) | 0.122 | 0.059 | 0.005 | 135 |

|  | GFR | ST2 (ng/mL) |
|---|---|---|

Correlation Matrix (R)

| GFR | 1.000 | 0.028 |
| ST2 (ng/mL) | 0.028 | 1.000 |

Correlation Significance (P)

| GFR | — | 0.748 |
| ST2 (ng/mL) | 0.748 | — |

TABLE 18

Pearson Correlation Results - Creatinine Clearance and ST2

Descriptive Statistics

| Variable | Mean | Std Dev. | Std Err | N |
|---|---|---|---|---|
| Screening Cr | 2.175 | 0.859 | 0.081 | 113 |
| ST2 (ng/mL) | 0.122 | 0.058 | 0.006 | 113 |

|  | Screening Cr | ST2 (ng/mL) |
|---|---|---|

Correlation Matrix (R)

| Screening Cr | 1.000 | −0.018 |
| ST2 (ng/mL) | −0.018 | 1.000 |

Correlation Significance (P)

| Screening Cr | — | 0.851 |
| ST2 (ng/mL) | 0.851 | — |

These results demonstrate that, as was expected in this population of subjects with chronic, managed renal insufficiency, there is no correlation between ST2 levels and either GFR (p=0.75) or creatinine clearance (p=0.851) in this population. This indicates that renal insufficiency, by itself, does not cause an elevation of ST2 levels.

The same analyses were carried out in a population of 139 subjects at the San Diego Veteran's Administration Hospital. All of the subjects had previously been diagnosed with acute decompensated heart failure (ADHF), and the mean ST2 level was about twice that seen in the population of patients with chronic renal insufficiency but no HF (see tables 17-18). There is an almost ubiquitous correlation between renal insufficiency and heart failure, with an almost 80% confluence of patients with stage III/IV HF also having impaired renal function (Fonarow and Heywood, Am. J. Med. (2006) 119(12A):S17-S25. Thus, because ADHF is correlated with ST2 levels, one would expect to see a correlation between renal insufficiency (as measured by GFR) and ST2 levels. This was exactly what was seen, as shown in Tables 19 and 20.

TABLE 19

Pearson Correlation Results - GFR and ST2 in ADHF

Descriptive Statistics

| Variable | Mean | Std Dev. | Std Err | N |
|---|---|---|---|---|
| GFR | 59.1 | 25.3 | 2.143 | 139 |
| ST2 (ng/mL) | 0.283 | 0.332 | 0.028 | 139 |

|  | GFR | ST2 (ng/mL) |
|---|---|---|

Correlation Matrix (R)

| GFR | 1.000 | −0.062 |
| ST2 (ng/mL) | −0.062 | 1.000 |

Correlation Significance (P)

| GFR | — | 0.470 |
| ST2 (ng/mL) | 0.470 | — |

TABLE 20

Pearson Correlation Results - GFR and ST2 Ratios in ADHF

Descriptive Statistics

| Variable | Mean | Std Dev. | Std Err | N |
|---|---|---|---|---|
| GFR | 59.1 | 25.3 | 2.143 | 139 |
| ST2 ratio | 1.038 | 3.038 | 0.258 | 139 |

|  | GFR | ST2 ratio |
|---|---|---|

Correlation Matrix ®

| GFR | 1.000 | −0.161 |
| ST2 ratio | −0.161 | 1.000 |

Correlation Significance (P)

| GFR | — | 0.058 |
| ST2 ratio | 0.058 | — |

These results demonstrate that, in subjects with ADHF, ST2 values, whether represented as a single level or a ratio, are correlated with measures of renal insufficiency, but are independent of the renal insufficiency.

Example 9

Risk of Mortality Correlates with ST2 Concentrations

The amount of increased risk of mortality was evaluated in the subjects who participated in the PRIDE study and the veterans in the population described in Example 8.

Both 0.2 and 0.7 ng/ml ST2 thresholds were evaluated across the entire population (Table 21) and the just the ADHF subset (Table 22). The biggest difference between the two thresholds is that the PPV increases and the NPV decreases for the 0.7 ng/ml threshold in both patient sets.

TABLE 21

% Mortality by ST2 level in PRIDE Cohort

|  | ST2 ≥ 0.7 | ST2 < 0.7 | ST2 ≥ 0.2 | ST2 < 0.2 |
|---|---|---|---|---|
| Total N | 146 | 447 | 317 | 275 |
| Mortality N | 52 | 41 | 88 | 5 |
| % Mortality | 35.6% | 9.2% | 27.8% | 1.8% |

The NPV for 0.2 ng/ml is 98.2% and for 0.7 ng/ml is 90.8% in this population.

TABLE 22

% Mortality by ST2 level in Subjects with ADHF

|  | ST2 ≥ 0.7 | ST2 < 0.7 | ST2 ≥ 0.2 | ST2 < 0.2 |
|---|---|---|---|---|
| Total N | 81 | 127 | 167 | 41 |
| Mortality N | 30 | 26 | 55 | 1 |
| % Mortality | 37.0% | 20.5% | 32.9% | 2.4% |

The NPV for 0.2 ng/ml is 97.6% and for 0.7 ng/ml is 79.5% in this cohort.

For the ST2 ratio from the VET study the results are shown in Table 23.

TABLE 23

% Mortality in Subjects with Chronic Renal Failure ST2 ratio

|  | ≥0.85 | <0.85 |
|---|---|---|
| N | 35 | 79 |
| Mortality | 8 | 3 |
| % Mort | 22.9% | 3.8% |

The NPV for this measurement is 96.2%.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying, a subject having undiagnosed chest pain or undiagnosed chest discomfort as having heart failure, the method comprising:
   (a) selecting a subject having undiagnosed chest pain or undiagnosed chest discomfort;
   (b) performing an immunoassay to determine a level of soluble ST2 in a biological sample from the selected subject;
   (c) performing an immunoassay to determine a level of one or more adjunct biomarkers selected from the group consisting of: N-terminal (NT)-pro-brain natriuretic peptide (BNP), BNP, NT-pro-atrial natriuretic peptide (ANP), proANP, and ANP in a biological sample from the selected subject;
   (d) comparing the level of soluble ST2 in the selected subject to a reference level of soluble ST2;
   (e) comparing the level of the one or more adjunct biomarkers in the selected subject to a reference level of the one or more adjunct biomarkers; and
   (f) identifying a selected subject having an elevation in the level of soluble ST2 compared to the reference level of soluble ST2 and an elevation in the level of the one or more adjunct biomarkers compared to the reference level of the one or more adjunct biomarkers as having heart failure by performing echocardiography.

2. The method of claim 1, wherein the reference level of soluble ST2 is a level of soluble ST2 in a subject that has no disease or has no acute disease.

3. The method of claim 1, wherein the reference level of soluble ST2 is a threshold level of soluble ST2.

4. The method of claim 1, wherein the subject in step (a) is previously undiagnosed.

5. The method of claim 1, wherein the biological sample in step (b) and step (c) comprises serum or plasma.

6. A method for identifying a subject having undiagnosed chest pain or undiagnosed chest discomfort as having heart failure, the method comprising:
   (a) selecting a subject having undiagnosed chest pain or undiagnosed chest discomfort;
   (b) performing an immunoassay to determine a level of soluble ST2 in a biological sample from the selected subject;
   (c) performing an immunoassay to determine a level of one or more adjunct biomarkers selected from the group consisting of: N-terminal (NT)-pro-brain natriuretic peptide (BNP), proBNP, BNP, NT-pro-atrial natriuretic peptide (ANT), proANP, and ANP in a biological sample from the selected subject;
   (d) comparing the level of soluble ST2 in the selected subject to a reference level of soluble ST2;
   (e) comparing the level of the one or more adjunct biomarkers in the selected subject to a reference level of the one or more adjunct biomarkers; and
   (f) identifying a selected subject having an elevation in the level of soluble ST2 compared to the reference level of soluble ST2 and an elevation in the level of the one or more adjunct biomarkers compared to the reference level of the one or more adjunct biomarkers as having heart failure by performing cardiac catheterization.

7. The method of claim 6, wherein the reference level of soluble ST2 is a level of soluble ST2 in a subject that has no disease or has no acute disease.

8. The method of claim 6, wherein the reference level of soluble ST2 is a threshold level of soluble ST2.

9. The method of claim 6, wherein the subject is previously undiagnosed.

10. The method of claim 1, wherein the method is performed in an outpatient clinic.

11. The method of claim 6, wherein the method is performed in an outpatient clinic.

12. The method of claim 1, wherein the immunoassay to determine the level of soluble ST2 is an enzyme-linked immunosorbant assay (ELISA).

13. The method of claim 11, wherein the ELISA is a sandwich ELISA.

14. The method of claim 1, wherein the immunoassay to determine the level of soluble ST2 utilizes a monoclonal antibody.

15. The method of claim 6, wherein the immunoassay to determine the level of soluble ST2 is an enzyme-linked immunosorbant assay (ELISA).

16. The method of claim 15, wherein the ELISA is a sandwich ELISA.

17. The method of claim 6, wherein the immunoassay to determine the level of soluble ST2 utilizes a monoclonal antibody.

18. The method of claim 14, wherein the immunoassay to determine the level of soluble ST2 utilizes two different monoclonal antibodies that specifically bind to soluble ST2.

19. The method of claim 17, wherein the immunoassay to determine the level of soluble ST2 utilizes two monoclonal antibodies that specifically bind to soluble ST2.

20. The method of claim 6, wherein the biological sample in step (b) and step (c) comprises serum or plasma.

21. The method of claim 1, wherein the subject has undiagnosed chest pain.

22. The method of claim 1, wherein the subject has undiagnosed chest discomfort.

23. The method of claim 6, wherein the subject has undiagnosed chest pain.

24. The method of claim 6, wherein the subject has undiagnosed chest discomfort.

\* \* \* \* \*

UNITED STATES PATENT AND TRADEMARK OFFICE
CERTIFICATE OF CORRECTION

PATENT NO. : 9,568,481 B2  
APPLICATION NO. : 13/282111  
DATED : February 14, 2017  
INVENTOR(S) : James V. Snider and Sven Jacobson Page 1 of 1

It is certified that error appears in the above-identified patent and that said Letters Patent is hereby corrected as shown below:

In the Claims

Column 31, Line 63, Claim 1, delete "identifying," and insert -- identifying --, therefor.

Column 32, Line 40, Claim 6, delete "(ANT)," and insert -- (ANP), --, therefor.

Column 32, Line 65, Claim 12, delete "immunosorbant" and insert -- immunosorbent --, therefor.

Column 32, Line 66, Claim 13, delete "claim 11," and insert -- claim 12, --, therefor.

Column 33, Line 6, Claim 15, delete "immunosorbant" and insert -- immunosorbent --, therefor.

Signed and Sealed this  
Second Day of May, 2017

Michelle K. Lee  
*Director of the United States Patent and Trademark Office*